| (12) | United States Patent | (10) Patent No.: US 10,488,554 B2 |
|---|---|---|
| | Pierik et al. | (45) Date of Patent: Nov. 26, 2019 |

(54) REAL-TIME METOCEAN SENSOR ARRAYS

(71) Applicant: Sofar Ocean Technologies, Inc., San Francisco, CA (US)

(72) Inventors: Anke Pierik, Montara, CA (US); Andrew Wheeler Gans, Aptos, CA (US); Tim Janssen, Montara, CA (US); Evan Shapiro, San Francisco, CA (US); Pieter Bart Smit, Stanford, CA (US)

(73) Assignee: Sofar Ocean Technologies, Inc., San Francisco, CA (US)

( * ) Notice: Subject to any disclaimer, the term of this patent is extended or adjusted under 35 U.S.C. 154(b) by 0 days.

(21) Appl. No.: 15/928,041

(22) Filed: Mar. 21, 2018

(65) Prior Publication Data

US 2018/0275313 A1    Sep. 27, 2018

Related U.S. Application Data

(60) Provisional application No. 62/474,422, filed on Mar. 21, 2017.

(51) Int. Cl.
*G01W 1/02* (2006.01)
*G01W 1/04* (2006.01)
(Continued)

(52) U.S. Cl.
CPC .............. *G01W 1/04* (2013.01); *G01S 19/13* (2013.01); *G01S 19/14* (2013.01); *H04R 1/44* (2013.01);
(Continued)

(58) Field of Classification Search
None
See application file for complete search history.

(56) References Cited

U.S. PATENT DOCUMENTS 4,429,652 A    2/1984  Stol
5,066,256 A *  11/1991 Ward, Sr. ................ B63B 22/08
                                                        114/328
(Continued)

FOREIGN PATENT DOCUMENTS

WO    2005012079 A1    2/2005
WO    2005012079 A1    10/2005
(Continued)

OTHER PUBLICATIONS

"TRIAXYS Directional Wave Buoy." and "Wave Current Monitoring." AXYS Technologies, Feb. 2, 2014, axystechnologies.com/products/triaxys-directional-wave-buoy/ and axystechnologies.com/solutions/wave-current-monitoring/.*
(Continued)

*Primary Examiner* — John Fitzgerald
*Assistant Examiner* — Alexander A Mercado
(74) *Attorney, Agent, or Firm* — Kolitch Romano LLP

(57) ABSTRACT

A real-time metocean sensor array system may include a one or more floating instruments each including geolocation capabilities and connected to a satellite communication network. In some examples, the floating instruments may further include an omnidirectional hydrophone. Motion and acoustical data gathered by the instruments may be converted by onboard processing logic into wave, current, and/or wind-related observations that may be communicated in real time and analyzed via a cloud-based system.

16 Claims, 10 Drawing Sheets

(51) Int. Cl.
G01S 19/13 (2010.01)
H04R 1/44 (2006.01)
G01S 19/14 (2010.01)
G01W 1/00 (2006.01)
G06N 3/08 (2006.01)

(52) U.S. Cl.
CPC ......... G01W 2001/006 (2013.01); G06N 3/08 (2013.01); Y02A 90/14 (2018.01)

(56) References Cited

U.S. PATENT DOCUMENTS

| | | | |
|---|---|---|---|
| D440,171 | S | 4/2001 | Berger-North et al. |
| 7,789,723 | B2 | 9/2010 | Dane et al. |
| 2005/0279268 | A1 | 12/2005 | Storteig et al. |
| 2006/0215019 | A1* | 9/2006 | Harper .................... B63B 22/16 348/81 |
| 2008/0148839 | A1 | 6/2008 | Tillotson et al. |
| 2008/0169975 | A1 | 6/2008 | Yee |
| 2009/0265104 | A1* | 10/2009 | Shroff .................. G01C 21/165 701/472 |
| 2011/0060525 | A1 | 3/2011 | Teng et al. |
| 2012/0095629 | A1* | 4/2012 | Fjellstad .............. G01V 1/3826 701/21 |
| 2012/0190256 | A1* | 7/2012 | Martzall ............... B63B 22/166 441/16 |
| 2013/0222115 | A1 | 8/2013 | Davoodi et al. |
| 2015/0025804 | A1 | 1/2015 | Jones et al. |

FOREIGN PATENT DOCUMENTS

| | | | |
|---|---|---|---|
| WO | 2013055207 | A1 | 4/2013 |
| WO | 2015187743 | A1 | 12/2015 |

OTHER PUBLICATIONS

U.S. Receiving Office, International Search Report and Written Opinion of the International Searching Authority in PCT/US2018/023661, dated Jul. 5, 2018, which is the international application to this U.S. application.

Lemon et al., "Acoustic Measurements of Wind Speed and Precipitation Over a Continental Shelf", article, Journal of Geophysical Research, published May 20, 1984, vol. 89, pp. 3462-3472, American Geophysical Union (AGU), Washington, D.C.

Farmer et al., "Observations of High Frequency Ambient Sound Generated by Wind", excerpt from the book Sea Surface Sound, published 1988, pp. 403-415, edited by B. R. Kerman, Kluwer Academic Publishers, Dordrecht, the Netherlands.

Vagle et al., "An Evaluation of the WOTAN Technique of Inferring Oceanic Winds from Underwater Ambient Sound", article, Journal of Atmospheric and Oceanic Technology, published Aug. 1990, vol. 7, pp. 576-595, American Meteorological Society (AMS), Boston, MA.

Ding et al., "Observations of Breaking Surface Wave Statistics", article, Journal of Physical Oceanography, published Jun. 1994, vol. 24, pp. 1368-1387, American Meteorological Society (AMS), Boston, MA.

Juszko et al., "Wind Stress from Wave Slopes Using Phillips Equilibrium Theory", article, Journal of Physical Oceanography, published Feb. 1995, vol. 25, pp. 185-203, American Meteorological Society (AMS), Boston, MA.

Felizardo et al., "Correlations between Ambient Noise and the Ocean Surface Wave Field", article, Journal of Physical Oceanography, published Apr. 1995, vol. 25, pp. 513-532, American Meteorological Society (AMS), Boston, MA.

Zedel et al., "Ocean Ambient Sound Instrument System: Acoustic Estimation of Wind Speed and Direction from a Subsurface Package", published Aug. 1999, vol. 16, pp. 1118-1126, American Meteorological Society (AMS), Boston, MA.

Ma et al., "Prediction of underwater sound levels from rain and wind", article, The Journal of the Acoustical Society of America, published Jun. 2005, vol. 117, pp. 3555-3565, Acoustical Society of America (ASA), Melville, NY.

Manasseh et al., "Passive Acoustic Determination of Wave-Breaking Events and Their Severity across the Spectrum", article, Journal of Atmospheric and Oceanic Technology, published Apr. 2006, vol. 23, pp. 599-618, American Meteorological Society (AMS), Boston, MA.

I. R. Young, "Directional spectra of hurricane wind waves", article, Journal of Geographic Research, published Aug. 29, 2006, vol. III, American Geophysical Union (AGU), Washington, D.C.

Thomson et al., "Waves and the equilibrium range at Ocean Weather Station P", article, Journal of Geophysical Research: Oceans, published Nov. 8, 2013, vol. 118, pp. 5951-5962, American Geophysical Union (AGU), Washington, D.C.

Hydrosphere, "Hydrosphere Company Profile", E&OE Sol_Pow_V.2.00_Dec_2012, dated Dec. 31, 2012, and could be located at http://hydrosphere.co/uk/datasheets/brochure/HydrospherePIP.pdf on May 22, 2018.

U.S. Receiving Office, International Search Report and Written Opinion of the International Searching Authority in PCT/US2018/023661, dated Jul. 5, 2018, which is an international application of Applicant Spoondrift Technologies, Inc. that shares the same priority as this U.S. application.

* cited by examiner

REAL-TIME METOCEAN SENSOR ARRAYS

CROSS-REFERENCES

This application claims the benefit under 35 U.S.C. § 119(e) of the priority of U.S. Provisional Patent Application Ser. No. 62/474,422, filed Mar. 21, 2017, the entirety of which is hereby incorporated by reference for all purposes.

STATEMENT REGARDING FEDERALLY SPONSORED RESEARCH OR DEVELOPMENT

The invention described herein was made with government support under grant number DE-AR0000514 awarded by the Advanced Research Projects Agency-Energy (ARPA-e) of the U.S. Department of Energy, and benefitted from additional support from the Office of Naval Research of the U.S. Navy under grant number N00014-16-1-2856. The government of the United States of America may have certain rights in the invention.

FIELD

This disclosure relates to systems and methods for remote measurement and monitoring of sensed meteorological and oceanographic characteristics associated with bodies of water.

INTRODUCTION

The marine boundary layer, loosely defined as the upper sixty meters (m) of the ocean and the lower 100 m of the atmosphere, is a region of intense global economic activity, including, e.g., global shipping, offshore industry, coastal recreation, marine renewable energy, and global fisheries. Ocean waves represent the dynamic interface between ocean and atmosphere, which constitute a principal component of ocean weather, and distribute energy to coastal areas around the world. High-fidelity observations and forecasts of wave dynamics are essential for efficiency and safety of our many economic activities in the ocean, both in coastal areas and pelagic zones. Moreover, improved sensor coverage and forecasting ability will lead to better understanding of global ocean dynamics and air-sea interaction, improve our ability to adapt to changes in ocean climatologies, and better predict the dynamics of our coastlines and coastal habitats.

Traditionally, ocean wave sensors are expensive, complex, and require special equipment to deploy and maintain. As a result, ocean wave sensor data is sparse everywhere, and practically nonexistent in the open ocean. Driven in part by this lack of data, operational wave forecasting models are entirely process-based, in essence numerically integrating a partial differential equation with approximations and parameterizations for non-conservative and nonlinear processes affecting the wave field. When applied over long distances and time (e.g., for remote swell arrivals) even small errors in approximations accumulate and can grow to be substantial (50-100% error in wave height is not unusual). As a consequence, local sensor data is often not available to communities, industries, and local governments that need them most, and without data constraints, model forecasts are often inaccurate.

SUMMARY

The present disclosure provides systems, apparatuses, and methods relating to floating metocean sensor systems. In some embodiments, a floatable metocean instrument may include a hull having a central cavity, the hull including: a symmetrical lower portion extending downward from a midsection of the hull, configured to be submerged when the instrument is deployed in a body of water and to provide a uniform directional response to surface currents and surface waves, and a polygonal upper portion extending upward from the midsection of the hull and including a plurality of ribs extending upward from the mid-section to define a plurality of substantially planar angled faces; a plurality of solar panels, each disposed on a respective one of the angled faces of the hull; an electronics box removably disposed within the central cavity of the hull, the electronics box having a body portion defining an interior enclosure which contains: a global positioning system (GPS) receiver, a satellite transceiver, and a power regulating circuit configured to charge a battery using energy collected by the solar panels; and a battery configured to receive power from the power regulating circuit and to supply power to the GPS receiver and the satellite transceiver; wherein the GPS receiver is configured to measure positions of the instrument in real time, and the satellite transceiver is configured to transmit information based on the positions of the instrument to a satellite.

In some embodiments, a buoyant metocean sensor unit may include a hull having an inner cavity; processing logic and a displacement sensor disposed in the inner cavity of the hull; and a hydrophone coupled to the hull; wherein the processing logic is configured to: receive acoustic data from the hydrophone and motion data from the displacement sensor; determine local wave characteristics based on the motion data; and determine, using a trained neural network, local wind characteristics based on the motion data and the acoustic data.

In some embodiments, a method of determining metocean characteristics of a body of water may include: establishing remote communication with a plurality of floating metocean sensor units deployed in a body of water, each of the floating metocean sensor units including a hull having an attached hydrophone and enclosing processing logic in communication with the hydrophone and an onboard displacement sensor; receiving wave information from each of the sensor units based on motion of the sensor unit as determined by the displacement sensor; and receiving wind information from each of the sensor units based on the wave information and a measurement of underwater sound using the hydrophone.

Features, functions, and advantages may be achieved independently in various embodiments of the present disclosure, or may be combined in yet other embodiments, further details of which can be seen with reference to the following description and drawings.

DETAILED DESCRIPTION

Figure 1:
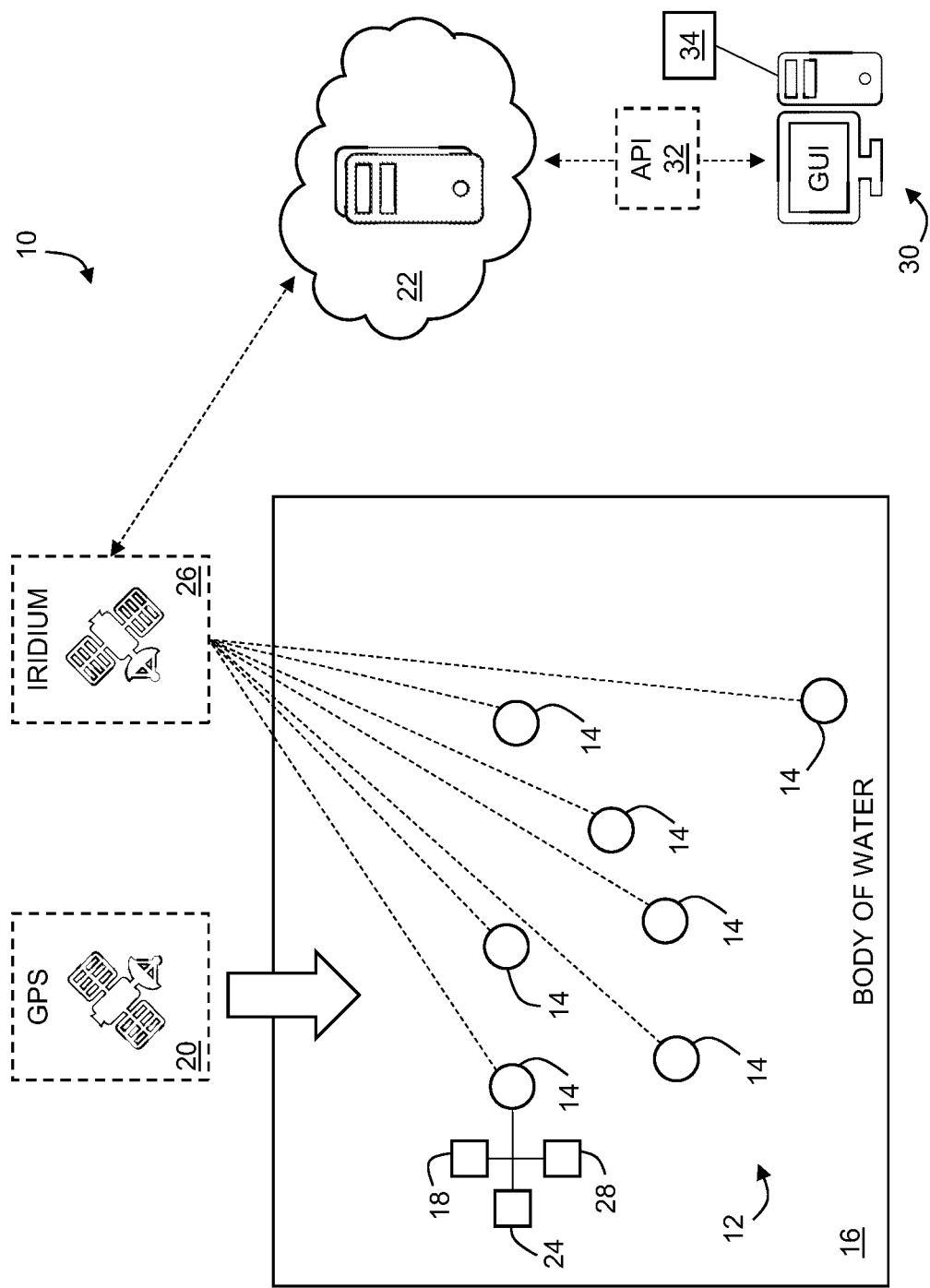
FIG. 1 is a schematic view of an illustrative metocean sensor array system in accordance with aspects of the present disclosure.

Various aspects and examples of real-time metocean sensor arrays, as well as related systems and methods, are described below and illustrated in the associated drawings. Unless otherwise specified, a sensor array system in accordance with the present teachings, and/or its various components may, but are not required to, contain at least one of the structures, components, functionalities, and/or variations described, illustrated, and/or incorporated herein. Furthermore, unless specifically excluded, the process steps, structures, components, functionalities, and/or variations described, illustrated, and/or incorporated herein in connection with the present teachings may be included in other similar devices and methods, including being interchangeable between disclosed embodiments. The following description of various examples is merely illustrative in nature and is in no way intended to limit the disclosure, its application, or uses. Additionally, the advantages provided by the examples and embodiments described below are illustrative in nature and not all examples and embodiments provide the same advantages or the same degree of advantages.

This Detailed Description includes the following sections, which follow immediately below: (1) Definitions; (2) Overview; (3) Examples, Components, and Alternatives; (4) Illustrative Combinations and Additional Examples; (5) Advantages, Features, and Benefits; and (6) Conclusion. The Examples, Components, and Alternatives section is further divided into subsections A through E, each of which is labeled accordingly.

Definitions

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional, unrecited elements or method steps.

Terms such as "first", "second", and "third" are used to distinguish or identify various members of a group, or the like, and are not intended to show serial or numerical limitation.

"AKA" means "also known as," and may be used to indicate an alternative or corresponding term for a given element or elements.

"Coupled" means connected, either permanently or releasably, whether directly or indirectly through intervening components, and is not necessarily limited to physical connection(s).

Overview

The dynamics of the air-sea interface, which is responsible for the exchange of momentum, heat, water, and gas between the atmosphere and ocean, is driven by the action of (e.g., breaking) ocean waves, surface winds, and precipitation. The measurement of meteorological and oceanographic (i.e., metocean) characteristics, such as wave and current motions, temperature, wind, precipitation, fog, and/or the like, can be important for understanding air-sea dynamics, quantifying ocean-atmosphere exchange processes, and improving weather and wave models. Although great progress has been made in remote satellite sensing technology, the coverage remains limited due to inherent limitations in space-time sampling, and generally coarse temporal resolution. Moreover, accurate interpretation of remote sensing data usually requires calibration with in-situ measurements, which are often not available.

In-situ observations are generally very accurate, and provide excellent temporal resolution, however, the instrumentation required can be cost prohibitive and burdensome to deploy and maintain. In particular, direct measurements of wind and waves have historically been costly and difficult. Direct measurement of surface winds, for example, are typically made with elevated anemometers on masts, which require larger platforms for stability, or spar-like buoy geometries. Marine-grade anemometers are relatively costly, wave-induced platform motions need to be corrected for in the measurements, and the elevated position of the anemometer makes it vulnerable. Further, due to their size and cost, traditional in-situ metocean (i.e., meteorological-oceanographic) platforms are usually moored to the seafloor, which requires large vessels and specialized crew to deploy and becomes increasingly complicated in deep-water regions.

Traditional in-situ wave sensors are also expensive, large and heavy, and difficult to operate. Because of their cost, they are almost always moored into place to maintain position and prevent loss. Due to their complexity and size, they tend to be serviced by skilled and specialized engineers and scientists, and require larger service vessels, e.g., equipped with an A-frame hoist, to deploy. Due to high deployment and maintenance costs these instruments will generally be deployed proximate developed coastal areas in limited water depth and where they can be reached more easily.

As a consequence, in-situ metocean data in general, and collocated wave-wind data in particular, is generally sparse, and almost non-existent in open ocean regions.

The present disclosure describes rapidly deployable, low-cost, distributed sensor networks comprising compact, autonomous, floating instruments, also referred to as sensor units, buoys, and/or drifters. Due to their lower cost and size, these instruments can be deployed from almost any size vessel, and enable new deployment strategies such as free-drifting arrays in inaccessible regions, high-density networks to create local data abundance for statistical processing, etc. As used herein, a real-time metocean sensor array can include one or more sensor units.

In general, and with reference to FIG. 1, a system 10 comprising a real-time metocean sensor array 12 in accordance with the present disclosure may include a plurality of free-floating sensor units 14 deployed in a body of water 16 (e.g., an ocean or portion thereof). Each sensor unit 14 may be configured to sense meteorological and/or oceanographic characteristics of its local environment, and to determine its geographical position using a plurality of onboard sensors 18. For example, onboard sensors 18 may include a global positioning system (GPS) receiver for determining latitude, longitude, and elevation from a GPS satellite network 20, a motion sensor, acoustical sensor (e.g., a hydrophone), conductivity sensor, temperature sensor, salinity sensor, and/or the like. Although a selected number of sensor units is shown in FIG. 1, more or fewer sensor units may be utilized, and array 12 may include different numbers of sensor units 14 at different times.

Each sensor unit 14 may further be configured to communicate with a computer network 22 or cloud via satellite communications. For example, sensor units 14 may have satellite communication modules 24 that include components such as a transceiver and modem configured to communicate with a communications satellite constellation 26 (e.g., the Iridium constellation). Although the GPS network and the Iridium constellation are depicted in FIG. 1, any suitable position/displacement and communication systems may be utilized. For example, with respect to the satellite modem, telemetry may be supplemented by (or changed to) one or more other types, such as radio frequency (RF) antenna, GSM (Global System for Mobile Communications)/GPRS (General Packet Radio Service) cellular modem, Bluetooth® wireless technology, and/or WiFi.

Sensor data is processed onboard each sensor unit 14, using processing logic 28. Processing logic 28 may include any suitable device or hardware configured to process data by performing one or more logical and/or arithmetic operations (e.g., executing coded instructions). For example, processing logic 28 may include one or more processors (e.g., central processing units (CPU) and/or graphics processing units (GPU)), microprocessors, clusters of processing cores, FPGAs (field-programmable gate arrays), artificial intelligence (AI) accelerators, digital signal processors, and/or any other suitable combination of logic hardware. Users may be granted access to the data, or a processed and/or aggregated version thereof, by accessing network 22 using, e.g., any suitable computing device 30. Access to the data may be accomplished substantially directly, for example, by organizing data received from the metocean sensor units into a database and providing access via an application programming interface (API) 32 provided for the purpose. Additionally or alternatively, the data may be aggregated and made accessible to the user through a front-end Web application portal.

A back-end software system comprising network 22 may include a data store (e.g., database) to receive, store, and organize data. In the depicted example, a computer software application 34 executed by computing device 30 and/or server(s) in cloud 22 provides a front-end user interface (UI, e.g., a graphical user interface or GUI), allowing the user to view, analyze, manipulate, or otherwise interact with information collected or transmitted by array 12. In addition, the software application may provide real-time information regarding system 10, such as a particular instrument's location and various other desired real-time features of the instrument and/or its surroundings. Substantially any information that can be transmitted by the instrument to satellite system 26, and/or anything that can be deduced or inferred from such information, can be displayed to the user by the software application.

The Web-based interface, and in some examples software application 34 via API 32, may allow the user to control various aspects of the instrument remotely. For example, the satellite transceiver of the instrument may be configured to transmit information regarding at least one setting of the instrument to the cloud via satellite, which may then permit access by the Web interface and/or computer software application. The Web interface and/or computer software application may be configured to display the instrument settings to the user, receive instructions to change the settings from the user, and transmit those instructions back to the instrument via the cloud and the satellite communication system. Non-limiting examples of instrument settings that might be changed remotely in this manner include power status of the instrument, data sampling rates, data update rates, strobe light activation and flash sequence, and on-instrument data processing, among others.

Furthermore, the Web interface and/or software application may be configured to generate a real-time alert and to display the alert on a graphical user interface, if user-defined conditions of the instrument are exceeded. In some examples, real-time alerts may be provided to the user in a different format, such as by email, text message, and/or the like. For example, the system may be configured to alert the user if particular wave or current magnitudes are exceeded, or the location of the instrument passes beyond some predetermined geographical boundary, or if the instrument malfunctions or stops functioning, among others. In some examples, remote firmware updates may be made to the sensor units via system 10, e.g., for on the fly adjustments of sensor functionality, onboard analysis, etc.

Aspects of metocean sensor array systems may be embodied as a computer method, computer system, or computer program product. Accordingly, aspects of the metocean sensor array system may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the metocean sensor array system may take the form of a computer program product embodied in a computer-readable medium (or media) having computer-readable program code/instructions embodied thereon.

Any combination of computer-readable media may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable non-transitory, tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device.

Program code embodied on a computer-readable medium may be transmitted using any appropriate medium, including but not limited to wireless, wireline, optical fiber cable, RF, and/or the like, and/or any suitable combination of these.

Computer program code for carrying out operations for aspects of the metocean sensor array system may be written in one or any combination of programming languages, including an object-oriented programming language such as Java, C++, and/or the like, and conventional procedural programming languages, such as C. Mobile apps may be developed using any suitable language, including those previously mentioned, as well as Objective-C, Swift, C#, HTML5, and the like. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of the metocean sensor array system are described herein with reference to block diagrams of methods, apparatuses, systems, and/or computer program products. Each block and/or combination of blocks in a block diagram may be implemented by computer program instructions. The computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block diagram block(s). In some examples, machine-readable instructions may be programmed onto a programmable logic device, such as a field programmable gate array (FPGA).

These computer program instructions can also be stored in a computer-readable medium that can direct a computer, other programmable data processing apparatus, and/or other device to function in a particular manner, such that the instructions stored in the computer-readable medium produce an article of manufacture including instructions which implement the function/act specified in the block diagram block(s).

The computer program instructions can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the block diagram block(s).

Any block diagram in the drawings is intended to illustrate the architecture, functionality, and/or operation of possible implementations of systems, methods, and computer program products according to aspects of the metocean sensor array system. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts.

Examples, Components, and Alternatives

The following sections describe selected aspects of exemplary real-time metocean sensor arrays, as well as related systems and/or methods. The examples in these sections are intended for illustration and should not be interpreted as limiting the entire scope of the present disclosure. Each section may include one or more distinct embodiments or examples, and/or contextual or related information, function, and/or structure.

A. Illustrative Sensor Units

As shown in FIGS. 2-9, this section describes an illustrative sensor unit 100 suitable for use with real-time metocean sensor arrays in accordance with the present disclosure. Sensor unit 100 is an example of sensor units 14, described above.

Figure 2:
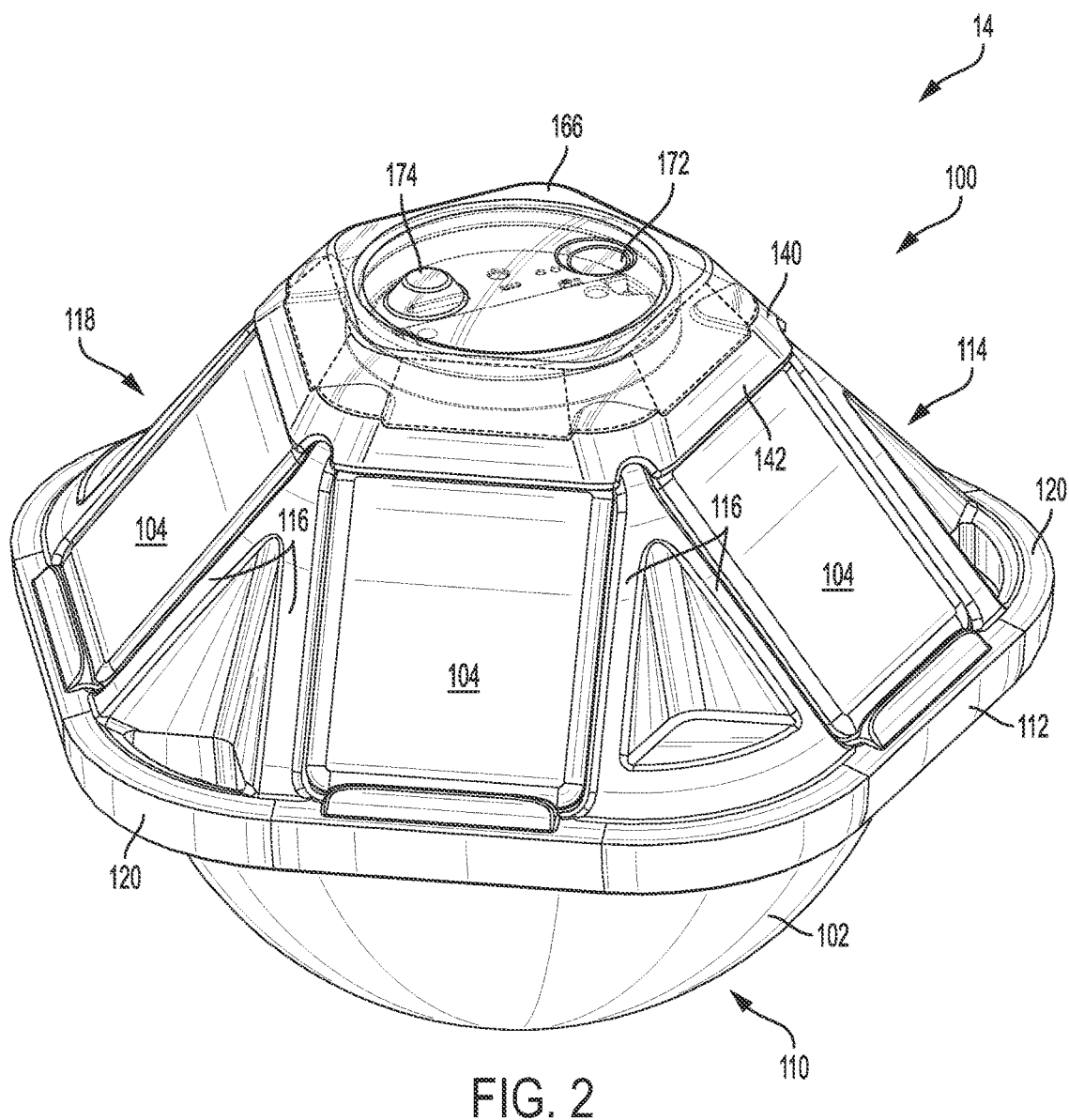
FIG. 2 is an isometric view of an illustrative sensor unit suitable for use in the system of FIG. 1.
Figure 3:
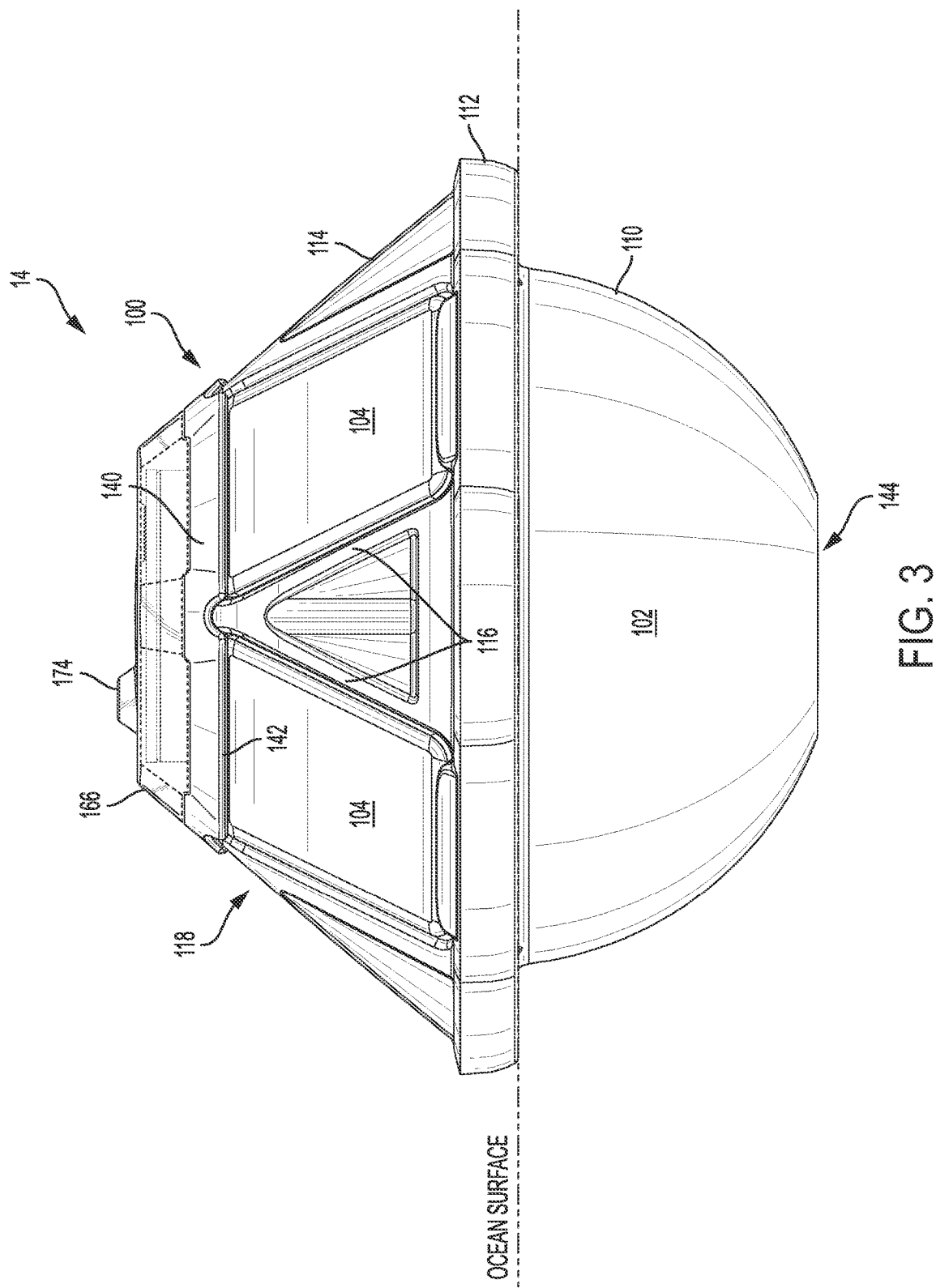
FIG. 3 is a side elevation view of the sensor unit of FIG. 2.
Figure 4:
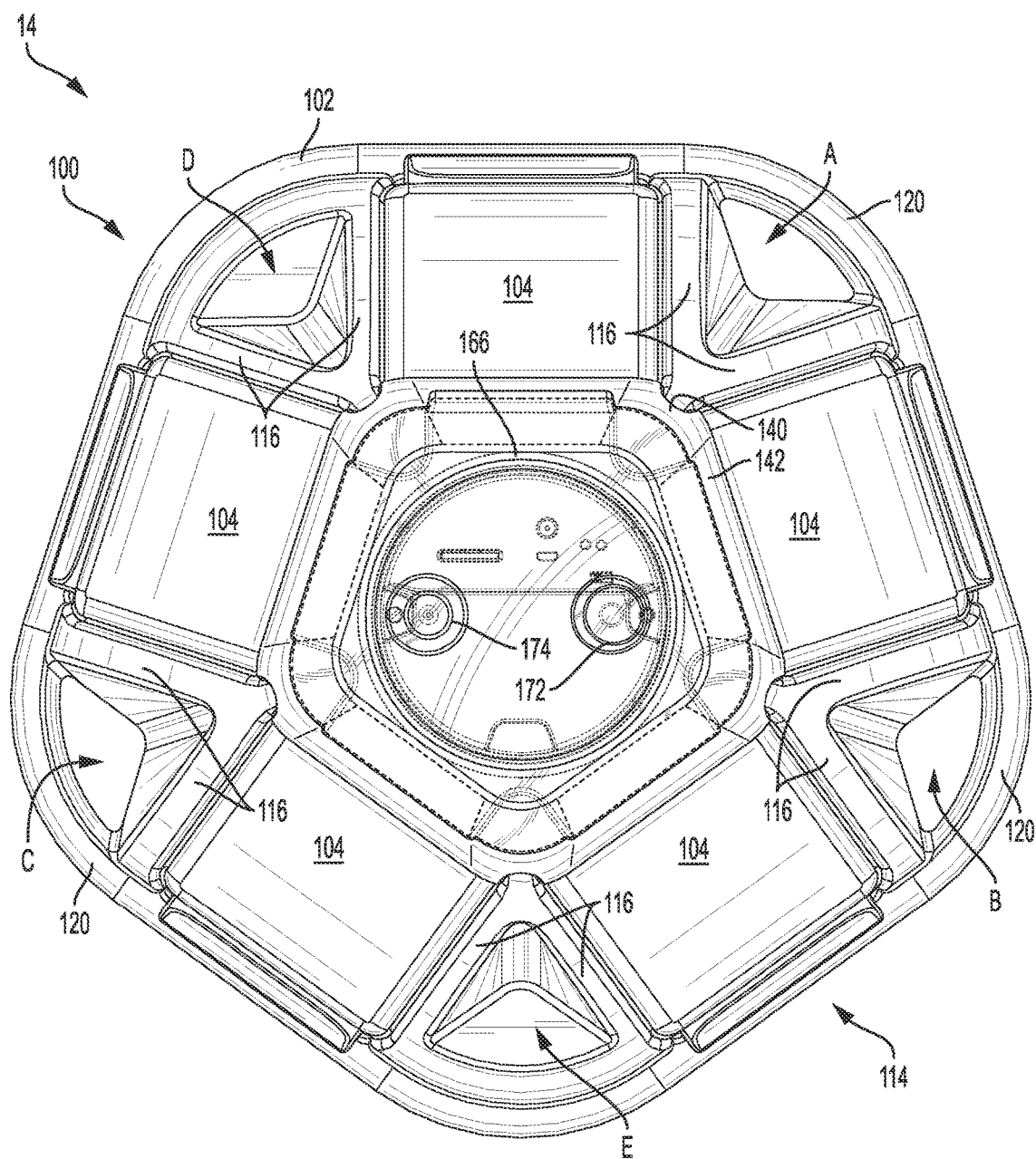
FIG. 4 is a top plan view of the sensor unit of FIG. 2.
Figure 5:
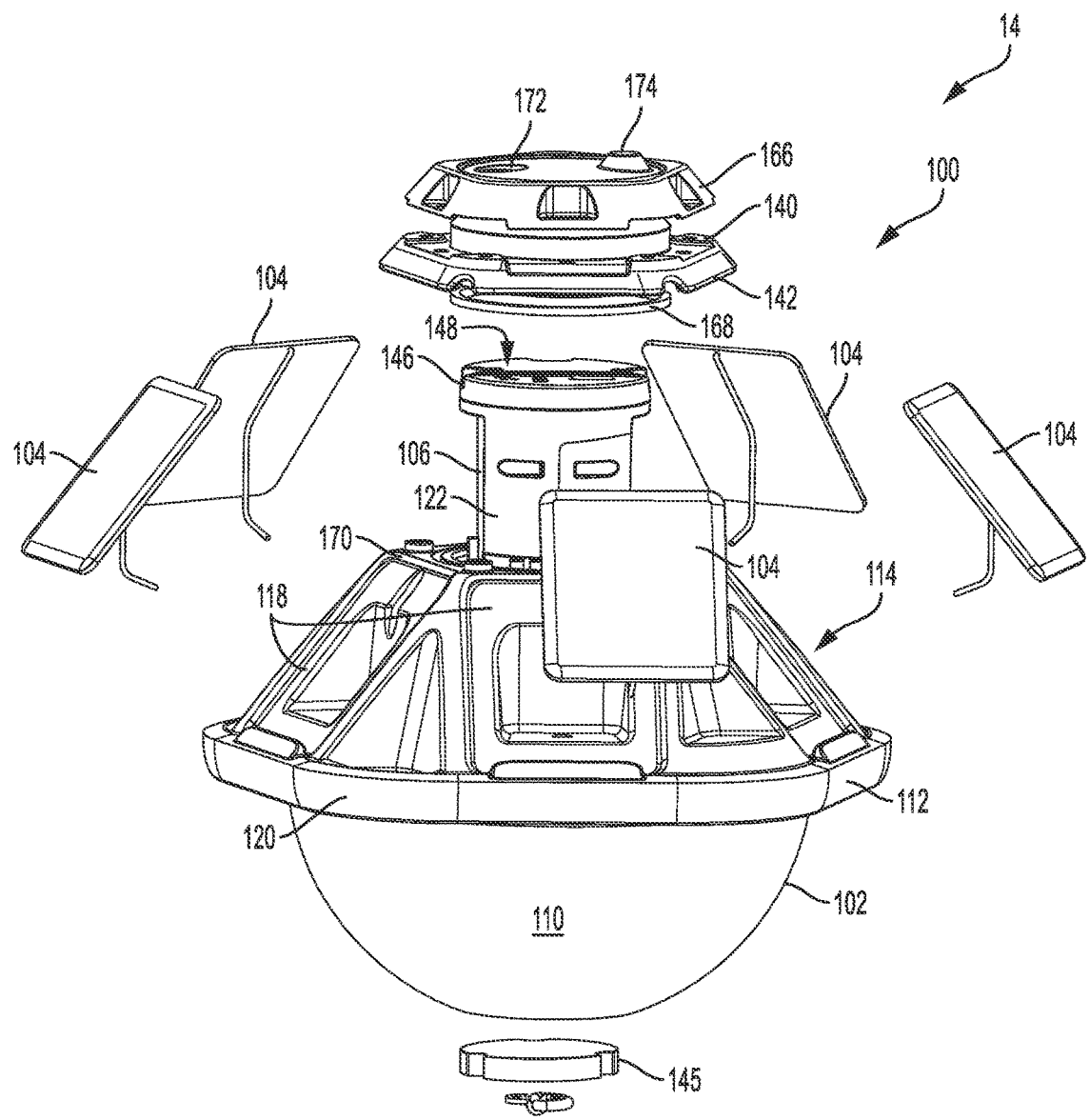
FIG. 5 is an isometric exploded view of the sensor unit of FIG. 2.
Figure 6:
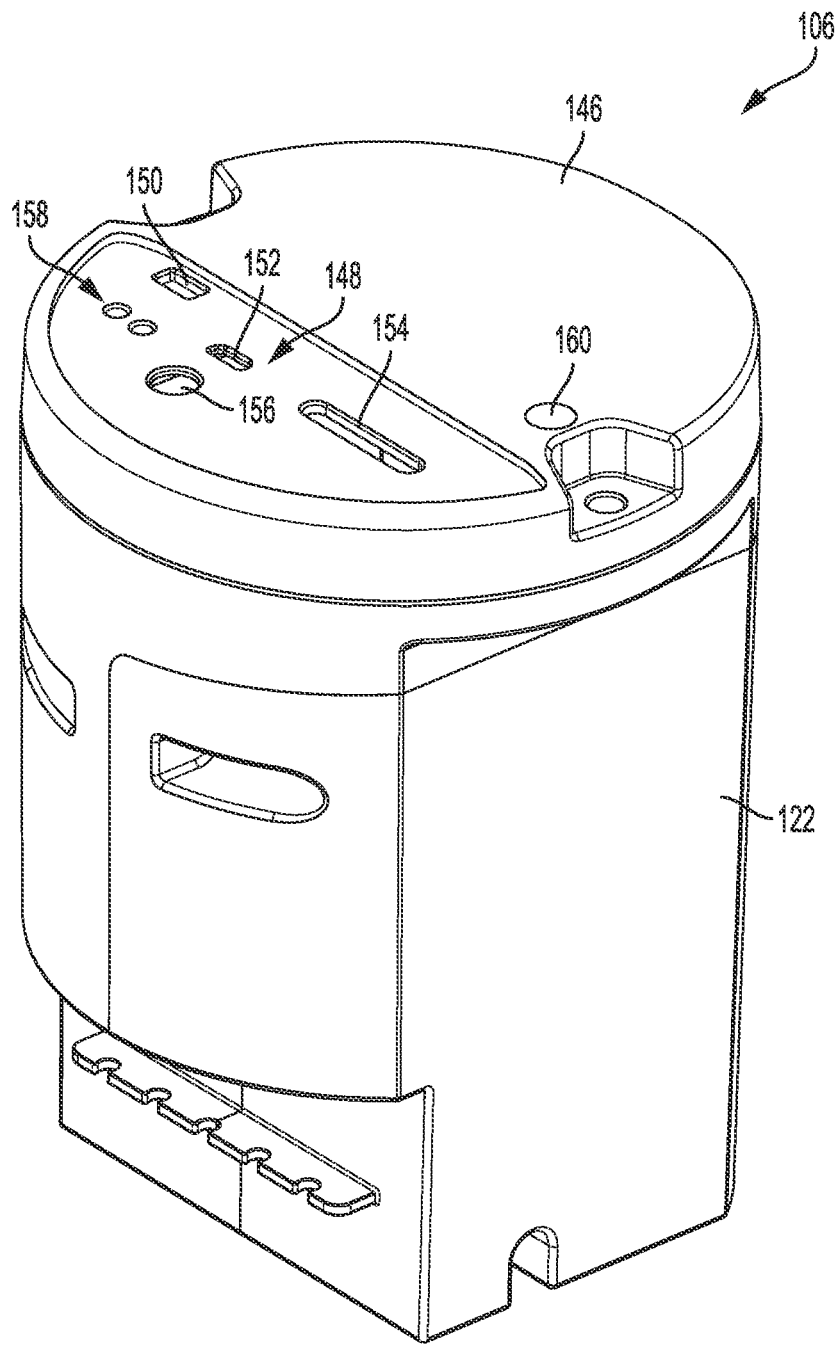
FIG. 6 is an isometric view of an electronics enclosure suitable for use with metocean sensor units described herein.
Figure 7:
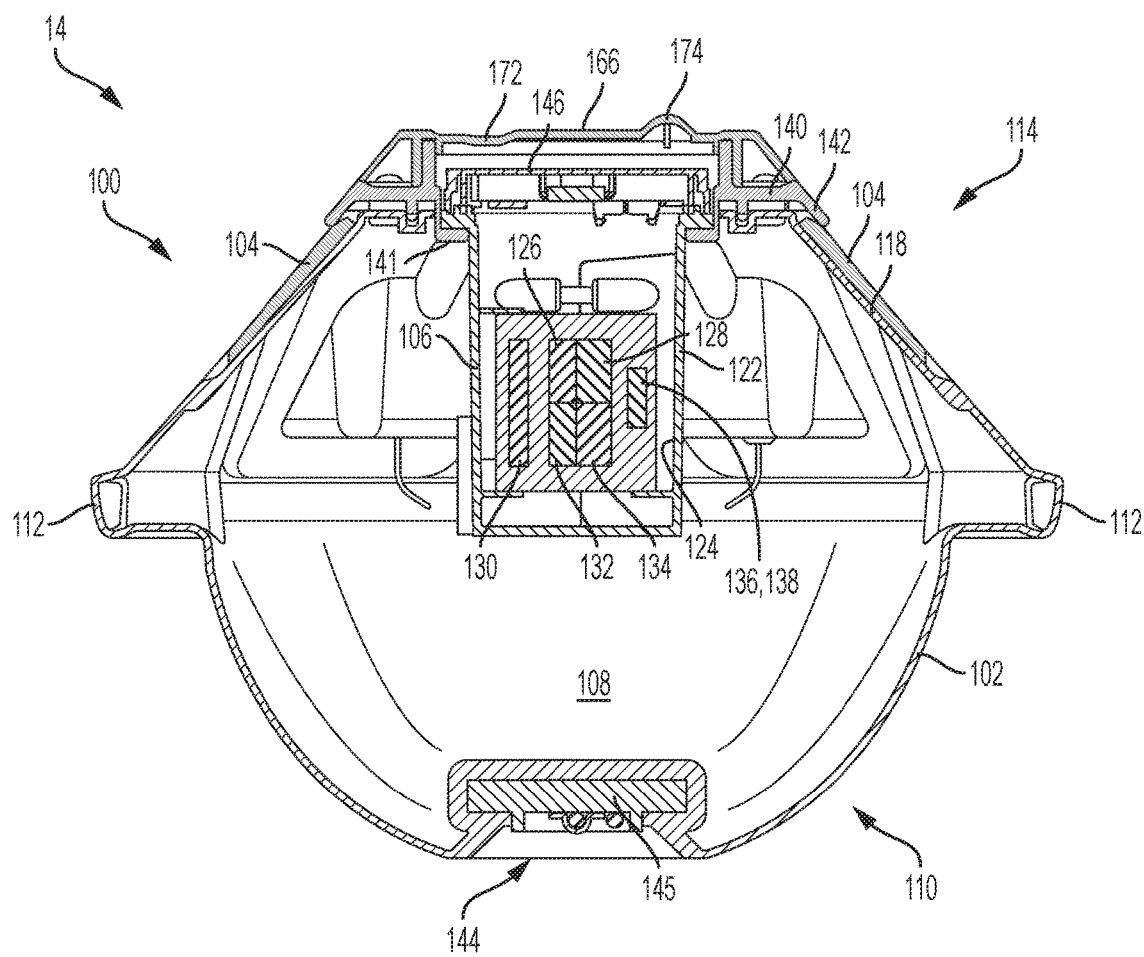
FIG. 7 is a sectional side elevation view of the sensor unit of FIG. 2.
Figure 9:
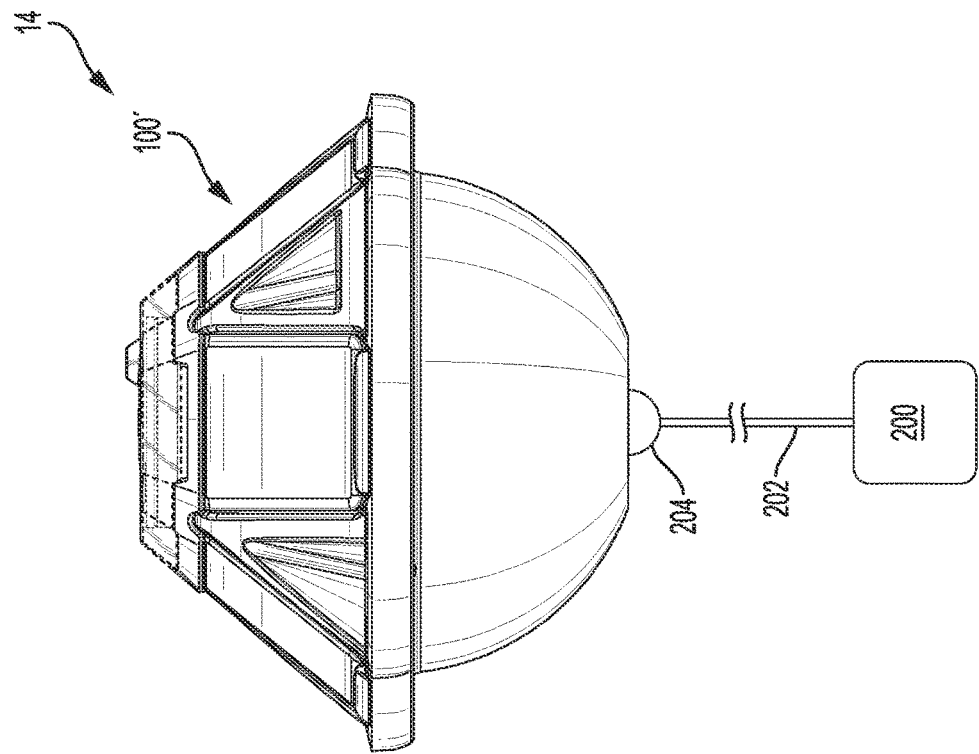
FIG. 9 is a side elevation view of the sensor unit of FIG. 8 with the hydrophone in an extended or deployed configuration.
Figure 8:
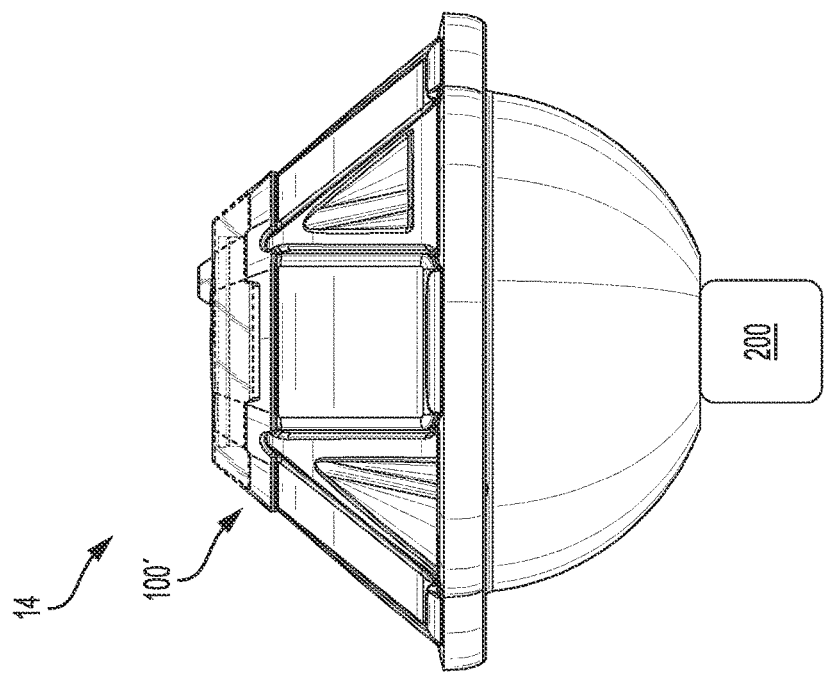
FIG. 8 is a side elevation view of another illustrative sensor unit having an attached hydrophone in accordance with aspects of the present disclosure.

FIG. 2 is an isometric view of sensor unit 100; FIG. 3 is a side elevation view of sensor unit 100; and FIG. 4 is an overhead plan view of sensor unit 100. FIG. 5 is an exploded view of the sensor unit; and FIG. 6 is an isometric view of a selected component thereof. FIG. 7 is a sectional view of sensor unit 100, showing relationships between internal components as assembled. Finally, FIGS. 8 and 9 are side elevation views of an embodiment of the sensor unit having an extendable/retractable hydrophone.

Sensor unit 100 is an ocean wave and current sensor that integrates a fast-sampling, high-fidelity motion sensing package, onboard analysis, and processing for directional wave spectra and surface drift. As described above, global connectivity is provided through a satellite network, such as the Iridium satellite constellation. Sensor unit 100 is a solar-powered sensor platform, in the form of an oceanographic buoy. In the depicted embodiment, sensor unit 100 has a 0.37-inch thick exterior hull constructed from marine-grade plastics, with a six-inch opening at the top of the buoy extending into a hollow inner cavity. The sensor unit is compact (e.g., approximately fifteen inches in diameter), lightweight (e.g., approximately twelve lbs.), and may be completely solar-powered. (All of these dimensions, as well as others, can be varied.) These characteristics enable deployments from small vessels, as well as sustained operation. As described in the Overview section, each sensor unit may be in communication with a cloud-based back end, which may integrate with a web-based dashboard and/or an API to provide endpoints for real-time data integration into models, remote two-way access by users, and other real-time applications.

As mentioned above, FIGS. 2-5 show various views of an instrument, i.e., sensor unit 100, for measuring metocean characteristics, such as ocean wave and current motions. Instrument 100 includes a hull 102, a plurality of solar panels 104 disposed on outer portions of the hull, and an electronics box 106 disposed inside the hull. An isometric view of electronics box 106 is depicted in FIG. 6.

Hull 102 is generally hollow, defining a central cavity 108, and includes a symmetrical lower portion 110 extending downward from a midsection of the hull, the midsection being generally defined by a perimetric flange 112. Lower portion 110 of the hull is configured and intended to be submerged when the instrument is deployed in a body of water (e.g., body of water 16). Furthermore, lower portion 110 is symmetrical around a vertical axis, to provide stability and a uniform directional response to ocean surface currents and surface waves. In the embodiments shown in the drawings of the present disclosure, lower portion 110 of hull 102 is depicted as a cap or a segment of a sphere. In other cases, the lower portion of the hull might take some other axially symmetric shape, such as a cylindrical or frustoconical section.

Hull 102 also includes a polygonal upper portion 114 extending upward from the midsection of the hull. More specifically, upper portion 114 in this example is substantially frusto-pyramidal in shape, although other shapes may be suitable. Upper portion 114 of the hull includes a plurality of ribs 116 extending upward in triangular pairs from flange 112 to define a plurality of substantially planar angled faces 118. In the embodiments shown in the drawings of the present disclosure, upper portion 114 of hull 102 is depicted as pentagonal, meaning it defines five angled faces 118. More generally, the upper portion of the hull can define any desired number planar faces, such as three, four, six, or eight, among others.

A corresponding number of solar panels 104 are each disposed on a respective one of angled faces 118 of hull 102. Angled faces 118 may be oriented to optimize collection of incident solar radiation over a predetermined range of latitudes, such as zero to seventy degrees latitude. For example, angled faces 118 may be oriented at an angle in the range of approximately thirty to approximately sixty degrees with respect to a horizontal plane. In some cases, angled faces 118 may be oriented at an angle of approximately fifty degrees with respect to a horizontal plane. In this example, the taper angle and width of the sides of the pentagonal shape (e.g., approximately eleven inches) accommodate five solar panels at a zenith angle to optimize global performance while maintaining sufficient space on the top section to fit the electronics.

The triangular structures formed by ribs 116 provide strength and rigidity to the hull structure, thus keeping the hull lightweight. As best shown in FIG. 4, material is removed, i.e., apertures are formed, at three of the five corners of flange 112 (marked A, B, and C) to provide handles 120 (AKA grab points) for the buoy. In other embodiments, more or fewer such handles may be provided. Handles 120 can be used for lifting the buoy, pulling it out of the water, attaching grab lines or other items, etc. In this example, the remaining two corners (marked D and E) are kept closed to enable additional attachments, sensors, and/or pressure testing.

As shown in FIGS. 5-7, electronics box 106 is removably disposed within an upper portion of central cavity 108 of the hull. The electronics box has a body portion 122 defining an interior enclosure 124 which contains various electronics components to accomplish the desired functions of the instrument. See FIG. 7. Specifically, electronics box 106 contains at least a displacement sensor such as a GPS receiver 126 or the like, a satellite transceiver 128, a battery 130 configured to supply power to the instrument, at least including to the GPS receiver and the satellite transceiver, and a power regulating circuit 132 configured to charge the battery using energy collected by the solar panels. In some cases, the electronics box also may contain an inertial measurement unit (IMU) 134. The physical arrangement of the components within the electronics box need not be limited to the arrangement depicted in FIG. 7, and can include, for example, vertically and/or horizontally stacked printed circuit boards containing the components in any desired arrangement or configuration. Furthermore, in some embodiments, battery 130 may be placed outside the electronics box (but still within hull 102) rather than inside the electronics box.

In some examples, the electronics box may be modular, such that different versions of the enclosure (e.g., containing different sensor packages) can be swapped into and out of the same sensor unit hull. For example, a user could obtain one sensor unit accompanied by both an Iridium-based electronics box and a GSM-based electronics box, and then utilize the appropriate electronics box depending on the deployment needs.

Although the sensor components shown in the accompanying drawings primarily include a GPS receiver, an IMU, and in some cases a hydrophone, other embodiments may include additional sensors such as digital cameras, temperature and/or salinity sensors, among others.

Generally speaking, GPS receiver 126 is configured to determine positions and displacement of the instrument in real time (e.g., the buoy's geographical position and elevation may be sampled at a rate of 2.5 Hz), and satellite transceiver 128 is configured to transmit information based on the positions and/or displacement of the instrument. The information transmitted may include raw position data and/or data which has been filtered, corrected, transformed into velocity or relative motion information, or otherwise processed before transmission to the satellite. A digital signal processor 136 (DSP) may be provided and programmed to perform such filtering, correction or transformation of the raw data. This processor may reside on a separate circuit board as depicted in FIG. 7, or it may be integrated into a circuit board that also contains additional components.

In some cases, digital signal processor 136 may be configured to use the motion data collected by the IMU to correct position determinations made by the GPS receiver. Alternatively or additionally, the digital signal processor may be configured to receive data collected by the GPS receiver and to transform the data into wave and current information, before the satellite transceiver transmits the wave and current information. In some embodiments, more than one digital signal processor may be provided within the electronics box, with each performing some of the desired functions of the instrument. In some embodiments, an AI accelerator 138 is included to provide onboard artificial intelligence capabilities (see section B).

In the depicted embodiments, upper portion 114 of hull 102 includes a top clamping ring 140. When instrument 100 is fully assembled, electronics box 106 is inserted through a central aperture in clamping ring 140 and suspended from an inboard lip 141 of the ring into central cavity 108 of the hull (see FIG. 7). The clamping ring is bolted, screwed, or otherwise fastened to hull 102, and includes an outer flange 142 that pins solar panels 104 in place at their top ends. More specifically, the five solar panels (e.g., each approximately 4.25"×5.5") are installed into recesses (AKA solar pads) between the vertical ribs. At the base of each recess there is a lip extruded from the hull which captures the bottom edge of the solar panel. The top edge of each solar panel is captured by flange 142, which clamps the panel in place. This arrangement results in no additional screw attachments penetrating the hull, and facilitates device assembly. Behind each solar panel, and as part of the solar pads, there is an indentation in the hull for the cable assembly to be threaded into main hull cavity 108. The solar panels are wired into the hull cavity (e.g., to the electronics box) through a cable gland inserted into a through-hull aperture at the base of each indentation.

In some examples, lower portion 110 of hull 102 includes a substantially planar bottom surface 144 (e.g., approximately 4.5 inches in diameter), allowing the instrument to be rested upon a flat surface, such as a table or deck, in a stable, upright position. A ballast plate 145 (e.g., a stainless steel ballast plate) may be molded into the bottom of the hull body. This integrated ballast plate provides an attachment point, e.g., for a D-ring, allowing the buoy to be connected to a mooring system. Other attachment mechanisms may be provided, either additionally or alternatively.

Electronics box 106 includes a lid 146 containing an integrated user interaction panel 148 (see FIG. 4). The user interaction panel may include a wide variety of user interface mechanisms, such as a power switch 150, a wired communications port 152, a memory slot 154, at least one status indicator light 156, and a charging port 158. In some cases, lid 146 may further contain a visibility strobe 160. In some examples, more or fewer mechanisms and features may be present.

With reference to FIG. 6, the exterior configuration of electronics box 106 is shown, including the user-interaction panel (top), and strain-release cut-outs for solar panel cables (near bottom). The interior electronics of the instrument are enclosed in the plastic cylindrical electronics box, which is attached to the clamping ring and suspended into the main buoy cavity. The box lid rests on a lip on the clamping ring inner diameter, and is attached, e.g., by two screws. Box 106 integrates the complete user interaction panel in its top lid, which faces outward, toward the user for ready accessibility.

Electronics box 106 includes a main rounded-square body with a circular lid. In some examples, the box houses one four-cell lithium-ion battery as well as two vertical printed circuit boards (PCBs) and one horizontal circuit board (PCB). The two vertical boards are the motherboard (housing the main processor) and the power regulating board (housing solar regulating electronics and battery charger). On top of the vertically stacked boards is a third PCB, which is horizontally mounted and sits underneath the electronics box lid. This horizontal PCB houses the GPS antenna, satellite telemetry antenna, switches, and user access panel.

In some examples, onboard motion sensors include a GPS receiver and an IMU. The GPS antenna is mounted on a ground plane of poured copper, integrated into the top PCB, to prevent multi-path distortion of the GPS signal. An Iridium satellite modem provides global telemetry. The user access panel includes an on/off switch, USB access port, nonvolatile memory (e.g., Secure Digital (SD) card), a wall charging port, and LED indicator lights for the battery charge levels and system status. A third LED light may be recessed into the electronics box lid, functioning as an on-water visibility strobe. A Hall effect sensor may also be included to switch the instrument between standby and operational settings using a small hand-held magnet. The LED lights, on/off switch, charging port, USB access port and SD drive are all accessible on top of the electronics box.

Instrument 100 further includes a transparent cover 166 attached to upper portion 114 of the hull and covering lid 146 of electronics box 106. A sealing member, such as a silicone gasket seal 168, may be disposed between transparent cover 166 and clamping ring 140, and/or between ring 140 and an upper lip 170 of the hull of the instrument (as depicted in FIG. 7), to prevent ingress of water into the electronics box and/or cavity 108. The transparent cover provides an easily removable main seal and visual access to the user interaction panel.

The transparent cover also may include various other features, such as an indentation 172 to accommodate a magnet that can be used to activate the instrument by triggering a Hall sensor (not shown). Specifically, indentation 172 may be a recess (e.g., approximately one inch in diameter) located directly above the Hall sensor to provide the user with an indication of where to hold the magnet for mode-switching, and minimize the distance (gap) to the sensor to optimize functionality. Additionally or alternatively, a refractive light pipe 174 may be configured to scatter light produced by the visibility strobe (e.g., to provide improved visibility from the side). In some examples, the lightpipe includes a short (e.g., approximately two inch) truncated-cone protrusion, located directly over the strobe LED. The truncated-cone has eight ribs which extend into a recess in the electronics box lid where the strobe LED sits. The lightpipe draws light from the surface mounted LED on the horizontally oriented PCB underneath the e-box lid to the surface of the plastic cover through refraction.

Turning now to FIGS. 8 and 9, a second embodiment of sensor unit 100 is depicted and generally indicated at 100'. Sensor unit 100' is substantially identical to sensor unit 100, as described above, with the addition of a retractable hydrophone 200. To collect underwater acoustics data, omnidirectional hydrophone 200 is suspended on a tether 202 from the hull of sensor unit 100', e.g., at approximately two meters below the ocean surface (see FIG. 9). A two-meter depth deployment may provide shielding, e.g., against radiated sound from surface splashes against the hull. Other configurations may include various deployment depths, direct in-hull mounted, and various flow shielding options. To reduce footprint while in storage or while being transported, tether 202 may be coiled up or wound on an in-hull reel in the pre-deployment phase. Hydrophone 200 may be configured to deploy automatically when in contact with water. The tether (AKA cable) may be integrated into the hull through a strain relief 204, which is flexible enough to allow Lagrangian movement of the hydrophone to prevent flow noise, and reduce strain on the connecting hull-surface.

The electronics of sensor unit 100' incorporate AI accelerator hardware and provide the processing power (DSP), bandwidth, and on-board memory to enable real-time data acquisition at hydrophone sampling rates on the order of 100s of kHz. This hardware is utilized in one or more of the algorithms described in the following section. The firmware is configured to provide power management to enable long-term deployment.

Real-Time Motion Acquisition System (RTMAS)

In some examples, a motion sensor package includes a single-frequency GPS receiver and Inertial Measurement Unit to record the instrument's position and orientation in real time. The depicted embodiments acquire ocean wave motion and surface current motion based on GPS measurements, leveraging the precision achieved by the single-frequency receiver with a properly tuned and integrated antenna. Some embodiments integrate this activity with the onboard IMU to further constrain motion dynamics, and include higher-order corrections due to, e.g., antenna offset and/or pitch and roll motion of the device.

The GPS receiver provides time-of-day and instantaneous three-dimensional position estimates (latitude, longitude, elevation), as well as three-dimensional Doppler velocities (u, v, w). The GPS contains various sources of noise, which may be filtered out either on board the instrument, via remote processing, or through a combination of local and remote processing. To obtain wave statistics for satellite transmission, the GPS data may be run through a spectral analysis to obtain spectral distribution of wave variance (energy), and directions. This analysis may be implemented onboard to reduce the data density, thereby enabling relatively low-bandwidth satellite communication of the data (e.g., bulk statistics) on a regular basis (e.g., every hour).

Any suitable displacement-based algorithm may be implemented onboard the sensor units, to estimate three-dimensional displacement of the sensor unit based on raw position and elevation output passed to the algorithm from the GPS receiver. The present system solves for positions while incorporating a "relaxation to a zero-mean" displacement record, utilizing a low-pass filter. This prevents build-up of large values in the displacement record, which would result in loss of precision and/or overflow of the variable memory allocation on the embedded system. This relaxation implementation enables the measurement of waves in the presence of mean displacements from currents, which facilitates use of the instrument as a free-drifting measuring device (in addition to a moored option), even in strong currents.

The time series wave signal data and spectral data may be encoded and stored in nonvolatile memory onboard the sensor unit. Integrated statistics may be transferred by the satellite modem to one or more servers, where the data is parsed and stored in the system's back end database. Sensor unit status information, e.g., including temperature, humidity, geographical position, system status, and solar intensity, may also be transmitted by the instrument's satellite modem to the cloud server(s). Data stored on the sensor unit (e.g., SD card) may also be retrieved by the user and manually uploaded to the cloud, where it will be unencrypted, quality-improved, parsed, and stored in the back-end database.

Exemplary Deployment

The following is an illustrative process for deploying one or more sensor units, such as sensor unit 100. To prepare a sensor unit for deployment, the user creates an account with system 10 and sets any deployment-specific instrument settings. The settings may include approximate water depth, sampling rates, data update rate, whether the instrument is free-floating or moored to the seafloor, etc. On the device side, the user activates the sensor unit, e.g., by turning the power switch on the electronics box to the "ON" position, and checks for successful startup as indicated by the LEDs. If successful, the user closes and secures the transparent lid, and the system is ready for deployment.

In transit to the deployment site, the user can check the status of the instrument by viewing the user LEDs. When onsite, the user can switch the instrument to active sampling mode by holding a magnet to the designated indentation in the lid, thereby triggering the Hall sensor and switching the system to active mode. The user can switch back to sleep mode by again triggering the Hall sensor with the magnet. Using this type of magnetic switch enables the user to prepare the system without needing to open or close the main seal while in transit or on the water.

The user then places the sensor unit into the water, either attached to a mooring system or free drifting. Depending on user settings, the visibility LED may flash continuously, or at night, or in periods of low light when the system is running, as a navigation warning for mariners.

B. Illustrative Wind Sensing Method

This section describes steps of an illustrative method for determining wind characteristics using one or more real-time, hydrophone-equipped, metocean sensor units, such as sensor unit 100' described above. Aspects of metocean sensor array systems described above may be utilized in the method steps described below. Where appropriate, reference may be made to components and systems that may be used in carrying out each step. These references are for illustration, and are not intended to limit the possible ways of carrying out any particular step of the method.

Metocean sensor units (and arrays thereof) may include an inverse wind sensing capability through integration of a near-surface omnidirectional hydrophone, utilizing one or more physics-based machine learning algorithms and low-power artificial intelligence (AI) hardware. The fusion of hydrophone observations with fast-sampling surface motion tracking provides a rich data set. Inverse wind sensing is described herein for estimating wind speed and stress. However, the same or similar hardware may be used in related applications, such as precipitation detection, vessel identification, and wave breaking dissipation.

The relation between wind speed and high-frequency ambient underwater sound is well established. Although the ambient underwater sound spectrum has numerous sources, including surface waves, global shipping, and biological contributions, the primary natural source of ocean ambient sound in the range from 500 Hz to 50 kHz is the resonant self-oscillation of bubbles trapped under water by breaking waves or precipitation. The relation between wind and underwater noise is indirect: the wind provides energy to the surface wave field, which grows, and eventually leads to wave breaking, which injects air bubbles under water that radiate sound. Generally, stronger winds result in more wave breaking, more bubbles, and thus higher noise levels. Other sound sources (e.g. nearby shipping, precipitation, biology, etc.) can affect the underwater noise spectrum, which can complicate application of a direct physics-based inversion from the acoustic signal alone. Through collocation with a surface motion-sensing package, which provides a high-fidelity estimate of the wave spectrum and the lowest-order directional moments, another proxy of wind speed and direction is available. The wind speed can be derived from wave spectrum energy levels in the equilibrium range, and the mean wave direction in that spectral range provides a proxy for the surface wind direction.

By combining collocated observations of underwater sound and surface waves two quasi-independent estimates for wind speed are obtained, as well as a wave-derived wind direction proxy. Algorithms are utilized to optimize the weighting between the two estimates, depending on the conditions and specifics of the sound and wave spectrum. Conceptually the wind speed estimate, u, can be expressed as:

$$u = F[u_a, u_w](\cos \theta_w, \sin \theta_w),$$

where F denotes the fusion operator that combines the underwater sound and equilibrium wave spectrum observations, $u_a$ denotes an acoustics-based wind-speed estimate, $u_w$ corresponds to a wave-based wind-speed estimate, and $\theta_w$ is the wave-derived mean wind-direction. Both conventional algorithms and machine learning algorithms may be used (separately or together) to fuse the acoustic- and wave-based wind speed estimates. This may be done in combination with available physics relations, or as a stand-alone process.

Instead of, or in addition to, using predetermined approximate relations that relate observed quantities to wind speed, the system can be trained to directly infer wind speed from the acoustic and motion data. Physics-based relations for wind inversion effectively fit a predetermined, simple relation to available observations. Through machine learning, the ANN system establishes an AI-based inversion function, which may enable it to infer nonobvious relationships. In some examples, the machine learning-based wind inversion and sensor fusion may be compared to or provided to the user in parallel with the physics-based inversion strategy.

As with the wave signal data, wind-related data may be encoded and stored in nonvolatile memory onboard the sensor unit. Integrated statistics may be transferred by the satellite modem to one or more servers, where the data is parsed and stored in the system's back end database. Again, data stored on the sensor unit (e.g., SD card) may also be retrieved by the user and manually uploaded to the cloud, where it will be unencrypted, quality-improved, parsed, and stored in the back-end database.

C. Illustrative Data Processing System

Figure 10:
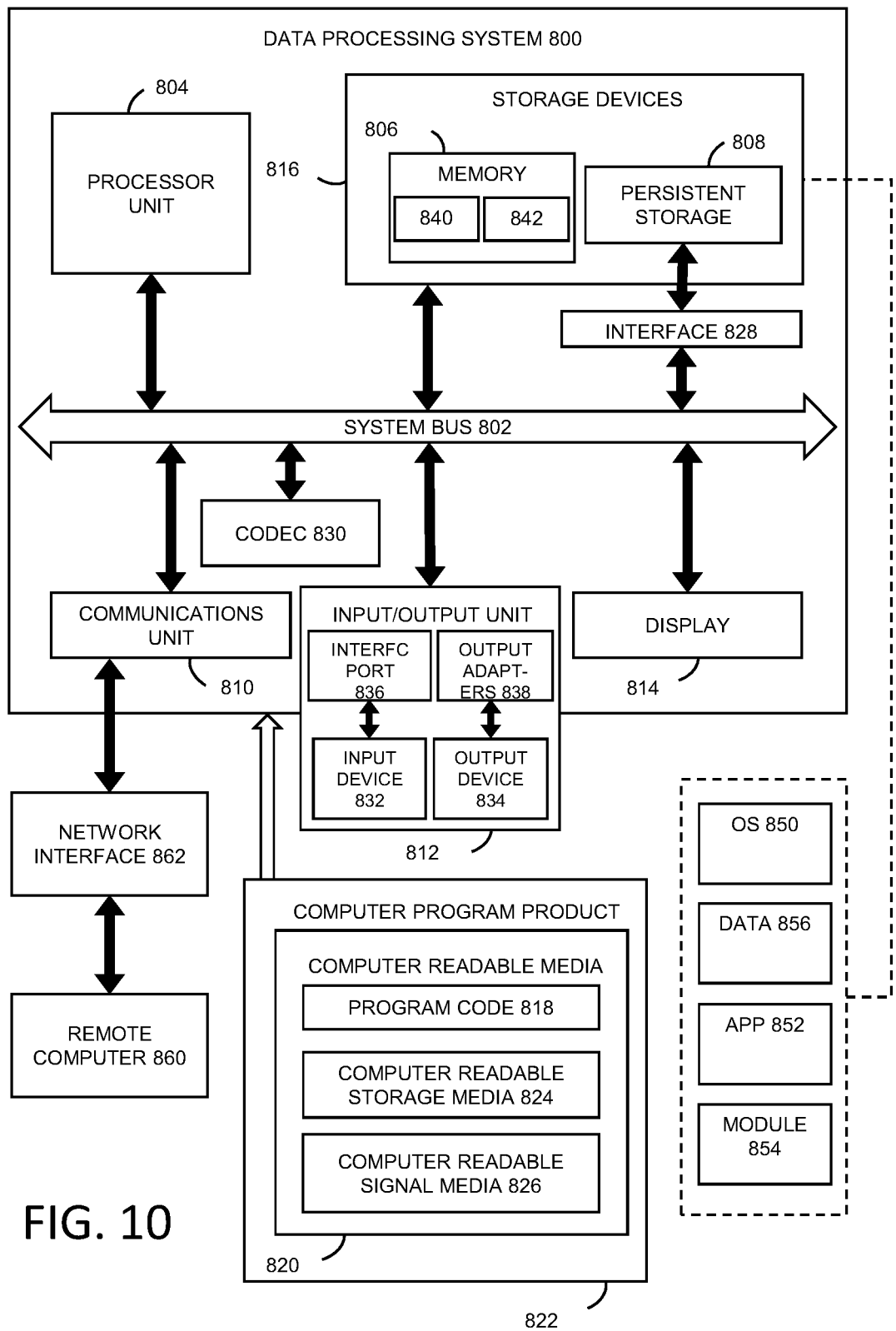
FIG. 10 is a schematic diagram of an illustrative data processing system suitable for use with aspects of the present disclosure.

As shown in FIG. 10, this example describes a data processing system 800 (also referred to as a computer, computing system, and/or computer system) in accordance with aspects of the present disclosure. In this example, data processing system 800 is an illustrative data processing system suitable for implementing aspects of the real-time metocean sensor array system. More specifically, in some examples, elements such as computing device 30 for accessing system data, a server in network 22 for storing and manipulating data, and/or processing logic onboard each of the sensor units, may be embodiments of data processing systems described in this section.

In this illustrative example, data processing system 800 includes a system bus 802 (also referred to as communications framework). System bus 802 may provide communications between a processor unit 804 (also referred to as a processor or processors), a memory 806, a persistent storage 808, a communications unit 810, an input/output (I/O) unit 812, a codec 830, and/or a display 814. Memory 806, persistent storage 808, communications unit 810, input/output (I/O) unit 812, display 814, and codec 830 are examples of resources that may be accessible by processor unit 804 via system bus 802.

Processor unit 804 serves to run instructions that may be loaded into memory 806. Processor unit 804 may comprise a number of processors, a multi-processor core, and/or a particular type of processor or processors (e.g., a central processing unit (CPU), graphics processing unit (GPU), etc.), depending on the particular implementation. Further, processor unit 804 may be implemented using a number of heterogeneous processor systems in which a main processor is present with secondary processors on a single chip. As another illustrative example, processor unit 804 may be a symmetric multi-processor system containing multiple processors of the same type.

Memory 806 and persistent storage 808 are examples of storage devices 816. A storage device may include any suitable hardware capable of storing information (e.g., digital information), such as data, program code in functional form, and/or other suitable information, either on a temporary basis or a permanent basis.

Storage devices 816 also may be referred to as computer-readable storage devices or computer-readable media. Memory 806 may include a volatile storage memory 840 and a non-volatile memory 842. In some examples, a basic input/output system (BIOS), containing the basic routines to transfer information between elements within the data processing system 800, such as during start-up, may be stored in non-volatile memory 842. Persistent storage 808 may take various forms, depending on the particular implementation.

Persistent storage 808 may contain one or more components or devices. For example, persistent storage 808 may include one or more devices such as a magnetic disk drive (also referred to as a hard disk drive or HDD), solid state disk (SSD), floppy disk drive, tape drive, Jaz drive, Zip drive, flash memory card, memory stick, and/or the like, or any combination of these. One or more of these devices may be removable and/or portable, e.g., a removable hard drive. Persistent storage 808 may include one or more storage media separately or in combination with other storage media, including an optical disk drive such as a compact disk ROM device (CD-ROM), CD recordable drive (CD-R Drive), CD rewritable drive (CD-RW Drive), and/or a digital versatile disk ROM drive (DVD-ROM). To facilitate connection of the persistent storage devices 808 to system bus 802, a removable or non-removable interface is typically used, such as interface 828.

Input/output (I/O) unit 812 allows for input and output of data with other devices that may be connected to data processing system 800 (i.e., input devices and output devices). For example, input device 832 may include one or more pointing and/or information-input devices such as a keyboard, a mouse, a trackball, stylus, touch pad or touch screen, microphone, joystick, game pad, satellite dish, scanner, TV tuner card, digital camera, digital video camera, web camera, and/or the like. These and other input devices may connect to processor unit 804 through system bus 802 via interface port(s) 836. Interface port(s) 836 may include, for example, a serial port, a parallel port, a game port, and/or a universal serial bus (USB).

Output devices 834 may use some of the same types of ports, and in some cases the same actual ports, as input device(s) 832. For example, a USB port may be used to provide input to data processing system 800 and to output information from data processing system 800 to an output device 834. Output adapter 838 is provided to illustrate that there are some output devices 834 (e.g., monitors, speakers, and printers, among others) which require special adapters. Output adapters 838 may include, e.g. video and sounds cards that provide a means of connection between the output device 834 and system bus 802. Other devices and/or systems of devices may provide both input and output capabilities, such as remote computer(s) 860. Display 814 may include any suitable human-machine interface or other mechanism configured to display information to a user, e.g., a CRT, LED, or LCD monitor or screen, etc.

Communications unit 810 refers to any suitable hardware and/or software employed to provide for communications with other data processing systems or devices. While communication unit 810 is shown inside data processing system 800, it may in some examples be at least partially external to data processing system 800. Communications unit 810 may include internal and external technologies, e.g., modems (including regular telephone grade modems, cable modems, and DSL modems), ISDN adapters, and/or wired and wireless Ethernet cards, hubs, routers, etc. Data processing system 800 may operate in a networked environment, using logical connections to one or more remote computers 860. A remote computer(s) 860 may include a personal computer (PC), a server, a router, a network PC, a workstation, a microprocessor-based appliance, a peer device, a smart phone, a tablet, another network note, and/or the like. Remote computer(s) 860 typically include many of the elements described relative to data processing system 800. Remote computer(s) 860 may be logically connected to data processing system 800 through a network interface 862 which is connected to data processing system 800 via communications unit 810. Network interface 862 encompasses wired and/or wireless communication networks, such as local-area networks (LAN), wide-area networks (WAN), and cellular networks. LAN technologies may include Fiber Distributed Data Interface (FDDI), Copper Distributed Data Interface (CDDI), Ethernet, Token Ring, and/or the like. WAN technologies include point-to-point links, circuit switching networks (e.g., Integrated Services Digital networks (ISDN) and variations thereon), packet switching networks, and Digital Subscriber Lines (DSL).

Codec 830 may include an encoder, a decoder, or both, comprising hardware, software, or a combination of hardware and software. Codec 830 may include any suitable device and/or software configured to encode, compress, and/or encrypt a data stream or signal for transmission and storage, and to decode the data stream or signal by decoding, decompressing, and/or decrypting the data stream or signal (e.g., for playback or editing of a video). Although codec 830 is depicted as a separate component, codec 830 may be contained or implemented in memory, e.g., non-volatile memory 842.

Non-volatile memory 842 may include read only memory (ROM), programmable ROM (PROM), electrically programmable ROM (EPROM), electrically erasable programmable ROM (EEPROM), flash memory, and/or the like, or any combination of these. Volatile memory 840 may include random access memory (RAM), which may act as external cache memory. RAM may comprise static RAM (SRAM), dynamic RAM (DRAM), synchronous DRAM (SDRAM), double data rate SDRAM (DDR SDRAM), enhanced SDRAM (ESDRAM), and/or the like, or any combination of these.

Instructions for the operating system, applications, and/or programs may be located in storage devices 816, which are in communication with processor unit 804 through system bus 802. In these illustrative examples, the instructions are in a functional form in persistent storage 808. These instructions may be loaded into memory 806 for execution by processor unit 804. Processes of one or more embodiments of the present disclosure may be performed by processor unit 804 using computer-implemented instructions, which may be located in a memory, such as memory 806.

These instructions are referred to as program instructions, program code, computer usable program code, or computer-readable program code executed by a processor in processor unit 804. The program code in the different embodiments may be embodied on different physical or computer-readable storage media, such as memory 806 or persistent storage 808. Program code 818 may be located in a functional form on computer-readable media 820 that is selectively removable and may be loaded onto or transferred to data processing system 800 for execution by processor unit 804. Program code 818 and computer-readable media 820 form computer program product 822 in these examples. In one example, computer-readable media 820 may comprise computer-readable storage media 824 or computer-readable signal media 826.

Computer-readable storage media 824 may include, for example, an optical or magnetic disk that is inserted or placed into a drive or other device that is part of persistent storage 808 for transfer onto a storage device, such as a hard drive, that is part of persistent storage 808. Computer-readable storage media 824 also may take the form of a persistent storage, such as a hard drive, a thumb drive, or a flash memory, that is connected to data processing system 800. In some instances, computer-readable storage media 824 may not be removable from data processing system 800.

In these examples, computer-readable storage media 824 is a non-transitory, physical or tangible storage device used to store program code 818 rather than a medium that propagates or transmits program code 818. Computer-readable storage media 824 is also referred to as a computer-readable tangible storage device or a computer-readable physical storage device. In other words, computer-readable storage media 824 is media that can be touched by a person.

Alternatively, program code 818 may be transferred to data processing system 800, e.g., remotely over a network, using computer-readable signal media 826. Computer-readable signal media 826 may be, for example, a propagated data signal containing program code 818. For example, computer-readable signal media 826 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 818 may be downloaded over a network to persistent storage 808 from another device or data processing system through computer-readable signal media 826 for use within data processing system 800. For instance, program code stored in a computer-readable storage medium in a server data processing system may be downloaded over a network from the server to data processing system 800. The computer providing program code 818 may be a server computer, a client computer, or some other device capable of storing and transmitting program code 818.

In some examples, program code 818 may comprise an operating system (OS) 850. Operating system 850, which may be stored on persistent storage 808, controls and allocates resources of data processing system 800. One or more applications 852 take advantage of the operating system's management of resources via program modules 854, and program data 856 stored on storage devices 816. OS 850 may include any suitable software system configured to manage and expose hardware resources of computer 800 for sharing and use by applications 852. In some examples, OS 850 provides application programming interfaces (APIs) that facilitate connection of different type of hardware and/or provide applications 852 access to hardware and OS services. In some examples, certain applications 852 may provide further services for use by other applications 852, e.g., as is the case with so-called "middleware." Aspects of present disclosure may be implemented with respect to various operating systems or combinations of operating systems.

The different components illustrated for data processing system 800 are not meant to provide architectural limitations to the manner in which different embodiments may be implemented. One or more embodiments of the present disclosure may be implemented in a data processing system that includes fewer components or includes components in addition to and/or in place of those illustrated for computer 800. Other components shown in FIG. 10 can be varied from the examples depicted. Different embodiments may be implemented using any hardware device or system capable of running program code. As one example, data processing system 800 may include organic components integrated with inorganic components and/or may be comprised entirely of organic components (excluding a human being). For example, a storage device may be comprised of an organic semiconductor.

In some examples, processor unit 804 may take the form of a hardware unit having hardware circuits that are specifically manufactured or configured for a particular use, or to produce a particular outcome or progress. This type of hardware may perform operations without needing program code 818 to be loaded into a memory from a storage device to be configured to perform the operations. For example, processor unit 804 may be a circuit system, an application specific integrated circuit (ASIC), a programmable logic device, or some other suitable type of hardware configured (e.g., preconfigured or reconfigured) to perform a number of operations. With a programmable logic device, for example, the device is configured to perform the number of operations and may be reconfigured at a later time. Examples of programmable logic devices include, a programmable logic array, a field programmable logic array, a field programmable gate array (FPGA), and other suitable hardware devices. With this type of implementation, executable instructions (e.g., program code 818) may be implemented as hardware, e.g., by specifying an FPGA configuration using a hardware description language (HDL) and then using a resulting binary file to (re)configure the FPGA.

In another example, data processing system 800 may be implemented as an FPGA-based (or in some cases ASIC-based), dedicated-purpose set of state machines (e.g., Finite State Machines (FSM)), which may allow critical tasks to be isolated and run on custom hardware. Whereas a processor such as a CPU can be described as a shared-use, general purpose state machine that executes instructions provided to it, FPGA-based state machine(s) are constructed for a special purpose, and may execute hardware-coded logic without sharing resources. Such systems are often utilized for safety-related and mission-critical tasks.

In still another illustrative example, processor unit 804 may be implemented using a combination of processors found in computers and hardware units. Processor unit 804 may have a number of hardware units and a number of processors that are configured to run program code 818. With this depicted example, some of the processes may be implemented in the number of hardware units, while other processes may be implemented in the number of processors.

In another example, system bus 802 may comprise one or more buses, such as a system bus or an input/output bus. Of course, the bus system may be implemented using any suitable type of architecture that provides for a transfer of data between different components or devices attached to the bus system. System bus 802 may include several types of bus structure(s) including memory bus or memory controller, a peripheral bus or external bus, and/or a local bus using any variety of available bus architectures (e.g., Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1394), and Small Computer Systems Interface (SCSI)).

Additionally, communications unit 810 may include a number of devices that transmit data, receive data, or both transmit and receive data. Communications unit 810 may be, for example, a modem or a network adapter, two network adapters, or some combination thereof. Further, a memory may be, for example, memory 806, or a cache, such as that found in an interface and memory controller hub that may be present in system bus 802.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

D. Illustrative Distributed Data Processing System

Figure 11:
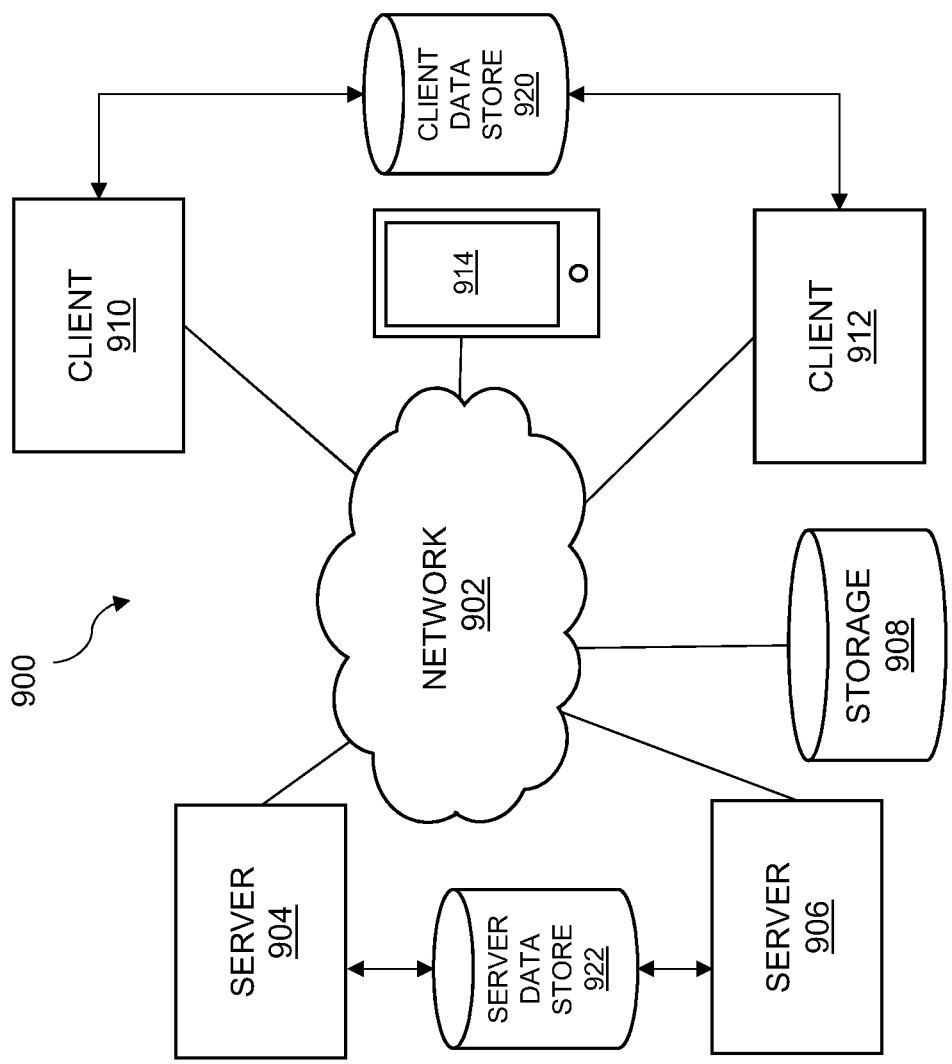
FIG. 11 is a schematic diagram of an illustrative computer network suitable for use with aspects of the present disclosure.

As shown in FIG. 11, this example describes a general network data processing system 900, interchangeably termed a computer network, a network system, a distributed data processing system, or a distributed network, aspects of which may be included in one or more illustrative embodiments of the real-time metocean sensor array system described herein. For example, cloud or network 22 may be an example of a distributed data processing system.

It should be appreciated that FIG. 11 is provided as an illustration of one implementation and is not intended to imply any limitation with regard to environments in which different embodiments may be implemented. Many modifications to the depicted environment may be made.

Network system 900 is a network of devices (e.g., computers), each of which may be an example of data processing system 800, and other components. Network data processing system 900 may include network 902, which is a medium configured to provide communications links between various devices and computers connected within network data processing system 900. Network 902 may include connections such as wired or wireless communication links, fiber optic cables, and/or any other suitable medium for transmitting and/or communicating data between network devices, or any combination thereof.

In the depicted example, a first network device 904 and a second network device 906 connect to network 902, as do one or more computer-readable memories or storage devices 908. Network devices 904 and 906 are each examples of data processing system 800, described above. In the depicted example, devices 904 and 906 are shown as server computers, which are in communication with one or more server data store(s) 922 that may be employed to store information local to server computers 904 and 906, among others. However, network devices may include, without limitation, one or more personal computers, mobile computing devices such as personal digital assistants (PDAs), tablets, and smartphones, handheld gaming devices, wearable devices, tablet computers, routers, switches, voice gates, servers, electronic storage devices, imaging devices, media players, and/or other networked-enabled tools that may perform a mechanical or other function. These network devices may be interconnected through wired, wireless, optical, and other appropriate communication links.

In addition, client electronic devices 910 and 912 and/or a client smart device 914, may connect to network 902. Each of these devices is an example of data processing system 800, described above regarding FIG. 8. Client electronic devices 910, 912, and 914 may include, for example, one or more personal computers, network computers, and/or mobile computing devices such as personal digital assistants (PDAs), smart phones, handheld gaming devices, wearable devices, and/or tablet computers, and the like. In the depicted example, server 904 provides information, such as boot files, operating system images, and applications to one or more of client electronic devices 910, 912, and 914. Client electronic devices 910, 912, and 914 may be referred to as "clients" in the context of their relationship to a server such as server computer 904. Client devices may be in communication with one or more client data store(s) 920, which may be employed to store information local to the clients (e.g., cookie(s) and/or associated contextual information). Network data processing system 900 may include more or fewer servers and/or clients (or no servers or clients), as well as other devices not shown.

In some examples, first client electric device 910 may transfer an encoded file to server 904. Server 904 can store the file, decode the file, and/or transmit the file to second client electric device 912. In some examples, first client electric device 910 may transfer an uncompressed file to server 904 and server 904 may compress the file. In some examples, server 904 may encode text, audio, and/or video information, and transmit the information via network 902 to one or more clients.

Client smart device 914 may include any suitable portable electronic device capable of wireless communications and execution of software, such as a smartphone or a tablet. Generally speaking, the term "smartphone" may describe any suitable portable electronic device configured to perform functions of a computer, typically having a touchscreen interface, Internet access, and an operating system capable of running downloaded applications. In addition to making phone calls (e.g., over a cellular network), smartphones may be capable of sending and receiving emails, texts, and multimedia messages, accessing the Internet, and/or functioning as a web browser. Smart devices (e.g., smartphones) may also include features of other known electronic devices, such as a media player, personal digital assistant, digital camera, video camera, and/or global positioning system. Smart devices (e.g., smartphones) may be capable of connecting with other smart devices, computers, or electronic devices wirelessly, such as through near field communications (NFC), Bluetooth®, WiFi, or mobile broadband networks. Wireless connectively may be established among smart devices, smartphones, computers, and/or other devices to form a mobile network where information can be exchanged.

Data and program code located in system 900 may be stored in or on a computer-readable storage medium, such as network-connected storage device 908 and/or a persistent storage 808 of one of the network computers, as described above, and may be downloaded to a data processing system or other device for use. For example, program code may be stored on a computer-readable storage medium on server computer 904 and downloaded to client 910 over network 902, for use on client 910. In some examples, client data store 920 and server data store 922 reside on one or more storage devices 908 and/or 808.

Network data processing system 900 may be implemented as one or more of different types of networks. For example, system 900 may include an intranet, a local area network (LAN), a wide area network (WAN), or a personal area network (PAN). In some examples, network data processing system 900 includes the Internet, with network 902 representing a worldwide collection of networks and gateways that use the transmission control protocol/Internet protocol (TCP/IP) suite of protocols to communicate with one another. At the heart of the Internet is a backbone of high-speed data communication lines between major nodes or host computers. Thousands of commercial, governmental, educational and other computer systems may be utilized to route data and messages. In some examples, network 902 may be referred to as a "cloud." In those examples, each server 904 may be referred to as a cloud computing node, and client electronic devices may be referred to as cloud consumers, or the like. FIG. 11 is intended as an example, and not as an architectural limitation for any illustrative embodiments.

E. Illustrative Combinations and Additional Examples

This section describes additional aspects and features of real-time metocean sensor arrays, presented without limitation as a series of paragraphs, some or all of which may be alphanumerically designated for clarity and efficiency. Each of these paragraphs can be combined with one or more other paragraphs, and/or with disclosure from elsewhere in this application, including the materials incorporated by reference in the Cross-References, in any suitable manner. Some of the paragraphs below expressly refer to and further limit other paragraphs, providing without limitation examples of some of the suitable combinations.

A0. A floatable metocean instrument comprising:
a hull having a central cavity, the hull including:
a symmetrical lower portion extending downward from a midsection of the hull, configured to be submerged when the instrument is deployed in a body of water and to provide a uniform directional response to surface currents and surface waves, and
a polygonal upper portion extending upward from the midsection of the hull and including a plurality of ribs extending upward from the mid-section to define a plurality of substantially planar angled faces;
a plurality of solar panels, each disposed on one of the angled faces of the hull;
an electronics box removably disposed within the central cavity of the hull, the electronics box having a body portion defining an interior enclosure which contains:
a GPS receiver,
a satellite transceiver, and
a power regulating circuit configured to charge a battery using energy collected by the solar panels; and
a battery configured to receive power from the power regulating circuit and to supply power to the GPS receiver and the satellite transceiver;
wherein the GPS receiver is configured to measure positions of the instrument in real time, and the satellite transceiver is configured to transmit information based on the positions of the instrument to a satellite.

A1. The instrument of paragraph A0, wherein the upper portion of the hull is pentagonal and includes exactly five substantially planar angled faces.

A2. The instrument of any of paragraphs A0 through A1, wherein the electronics box further contains an inertial measurement unit (IMU) configured to collect motion data, and a digital signal processor configured to use the motion data collected by the IMU to correct measurements made by the GPS receiver.

A3. The instrument of any of paragraphs A0 through A2, wherein the upper portion of the hull includes a clamping ring, and wherein the electronics box is suspended from the clamping ring into the central cavity of the hull.

A4. The instrument of paragraph A3, wherein the clamping ring comprises a perimetric flange configured to clamp an upper edge of each of the solar panels against the hull when the clamping ring is fastened to the hull.

A5. The instrument of any of paragraphs A0 through A4, wherein the electronics box further contains processing logic configured to receive data collected by the GPS receiver and to transform the data into wave and current information, and wherein the satellite transceiver is configured to transmit the wave and current information to the satellite.

A6. The instrument of any of paragraphs A0 through A5, wherein the lower portion of the hull includes a planar bottom surface.

A7. The instrument of any of paragraphs A0 through A6, wherein the electronics box includes a lid portion containing an integrated user interaction panel, and wherein the user interaction panel includes a power switch, a wired communications port, a memory slot, at least one status indicator light, and a charging port.

A8. The instrument of paragraph A7, wherein the lid portion further contains a visibility strobe.

A9. The instrument of paragraph A8, further comprising a transparent cover attached to the upper portion of the hull and covering the lid portion of the electronics box, the transparent cover including a refractive light pipe configured to scatter light produced by the visibility strobe.

A10. The instrument of any of paragraphs A0 through A9, wherein the angled faces of the hull are oriented approximately thirty to approximately sixty degrees with respect to a horizontal plane.

A11. The instrument of any of paragraphs A0 through A10, the midsection of the instrument further comprising a polygonal perimetric flange, wherein a handle is formed by an opening passing through the hull adjacent a corner of the perimetric midsection flange.

B0. A system for collecting and analyzing metocean data, comprising:
an instrument according to any of the previous numbered paragraphs;
a computer server configured to receive the information sent to the satellite by the satellite transceiver and to store the information; and
a computer software application configured to access information stored on the computer server and to make the information stored on the computer server available to a user through a graphical user interface.

B1. The system of paragraph B0, wherein the satellite transceiver is configured to transmit information regarding at least one setting of the instrument to the satellite.

B2. The system of paragraph B1, wherein the satellite transceiver is configured to receive instructions to change a setting of the instrument from the satellite and to transmit the instructions to the instrument.

B3. The system of paragraph B2, wherein the instrument includes a digital signal processor configured to control settings of the instrument based on instructions received from the satellite transceiver.

B4. The system of paragraph B2, wherein the computer software application is configured to display the setting to the user, receive instructions to change the setting from the user, and transmit the instructions to the server, and wherein the server is configured to transmit the instructions to the satellite.

B5. The system of any of paragraphs B0 through B4, wherein the computer software application is configured to generate a real-time alert and to display the alert on the graphical user interface, if user-defined conditions of the instrument are exceeded.

C0. A method of collecting and viewing ocean wave and current information, comprising:
deploying an instrument according to any of the preceding numbered paragraphs;
transmitting information based on position data collected by the instrument to a satellite;
transmitting the information from the satellite to a computer server; and
providing a computer software application configured to access information stored on the server and to make the information stored on the server available to a user through a graphical user interface.

C1. The method of paragraph C0, further comprising:
receiving instructions from the user through the graphical user interface to change a setting of the instrument;
transmitting the instructions received through the graphical user interface to the computer server;
transmitting the instructions from the computer server to the satellite;
transmitting the instructions from the satellite to the instrument; and
changing a setting of the instrument based on the instructions received from the satellite.

C2. The method of any of paragraphs C0 through C1, further comprising alerting the user through the graphical user interface if user-defined conditions of the instrument are exceeded.

C3. The method of any of paragraphs C0 through C2, further comprising storing information based on position data collected by the instrument on a digital memory device disposed within the instrument, retrieving the stored information, and transmitting the stored information to the computer server.

D0. A method of determining metocean characteristics of a body of water, the method comprising:
establishing remote communication with a plurality of floating metocean sensor units deployed in a body of water, each of the floating metocean sensor units including a hull having an attached hydrophone and enclosing processing logic in communication with the hydrophone and an onboard geolocation device;
receiving wave information from each of the sensor units based on motion of the sensor unit as determined by the respective geolocation device; and
receiving wind information from each of the sensor units based on the wave information and a measurement of underwater sound using the hydrophone.

D1. The method of D0, wherein establishing remote communication comprises communication via a satellite communication network.

D2. The method of any of paragraphs D0 through D1, wherein each of the floating metocean sensor units has an axially symmetric lower portion and a frusto-pyramidal upper portion.

D3. The method of D2, wherein a plurality of solar panels are attached to the upper portion of the hull.

D4. The method of D2, wherein the lower portion is substantially spherical.

D5. The method of any of paragraphs D0 through D4, wherein each of the sensor units is free floating in the body of water.

D6. The method of any of paragraphs D0 through D5, wherein the attached hydrophone is internal to the hull.

D7. The method of any of paragraphs D0 through D6, wherein the attached hydrophone is tethered to the hull.

D8. The method of D7, wherein a tether of the hydrophone is retractable into the hull.

E0. A buoyant metocean sensor unit comprising:
  a hull having a hemispherical lower portion, a frusto-pyramidal upper portion, and an inner cavity, a plurality of solar panels coupled to respective flat faces of the upper portion;
  an electronics enclosure mounted in the inner cavity of the hull, the electronics enclosure housing processing logic and a global positioning system (GPS) receiver;
  a rechargeable battery coupled to the electronics enclosure and configured to be recharged by the solar panels; and
  a hydrophone coupled to the hull;
  wherein the processing logic is configured to:
    receive acoustic data from the hydrophone and motion data from the GPS receiver;
    determine local wave characteristics based on the motion data; and
    determine, using a trained neural network, local wind characteristics based on the motion data and the acoustic data.

E1. The sensor unit of E0, wherein the trained neural network is configured to combine an acoustic-based wind speed estimate with a wave motion-based wind speed estimate.

E2. The sensor unit of any of paragraphs E0 through E1, wherein the trained neural network is configured to infer wind speed based only on the acoustic and motion data.

E3. The sensor unit of any of paragraphs E0 through E2, further comprising an inertial measurement unit (IMU) housed in the electronics enclosure.

E4. The sensor unit of E3, wherein the processing logic is further configured to correct the motion data using input from the IMU.

E5. The sensor unit of any of paragraphs E0 through E4, wherein the processing logic is further configured to determine local current characteristics based on the motion data.

E6. The sensor unit of any of paragraphs E0 through E5, wherein the hydrophone is omnidirectional.

E7. The sensor unit of any of paragraphs E0 through E6, wherein the hull is free-floating in a body of water.

E8. The sensor unit of any of paragraphs E0 through E7, wherein the hull is tethered to a floor of the body of water.

E9. The sensor unit of any of paragraphs E0 through E8, wherein the hydrophone is coupled to the hull by a cable.

E10. The sensor unit of any of paragraphs E0 through E9, wherein the hydrophone is contained within the hull.

E11. The sensor unit of any of paragraphs E0 through E10, further comprising a perimetral flange disposed between the upper portion of the hull and the lower portion of the hull.

E12. The sensor unit of E11, wherein the perimetral flange is polygonal.

E13. The sensor unit of E11, wherein a portion of the perimetral flange comprises a handle.

E14. The sensor unit of any of paragraphs E0 through E13, further comprising an upper clamp ring configured to clamp upper ends of each of the solar panels against the hull when the upper clamp ring is fastened to the hull.

E15. The sensor unit of E14, wherein the upper clamp ring further comprises a central aperture configured to support the electronics enclosure suspended within the inner cavity of the hull.

E16. The sensor unit of any of paragraphs E0 through E15, further comprising a transceiver configured to transmit information corresponding to the local wave characteristics and the local wind characteristics to a server using a wireless network.

E17. The sensor system of E16, wherein the wireless network comprises the Iridium satellite constellation.

F0. A buoyant metocean sensor unit comprising: a hull having an inner cavity; processing logic and a displacement sensor disposed in the inner cavity of the hull; and a hydrophone coupled to the hull; wherein the processing logic is configured to: receive acoustic data from the hydrophone and motion data from the displacement sensor; determine local wave characteristics based on the motion data; and determine, using a trained neural network, local wind characteristics based on the motion data and the acoustic data.

F1. The sensor unit of F0, wherein the trained neural network is configured to combine an acoustic-based wind speed estimate with a wave motion-based wind speed estimate.

F2. The sensor unit of any of paragraphs F0 through F1, wherein the displacement sensor comprises an inertial measurement unit (IMU).

F3. The sensor unit of any of paragraphs F0 through F2, wherein the displacement sensor comprises a global positioning system (GPS) receiver.

F4. The sensor unit of any of paragraphs F0 through F3, wherein the displacement sensor is a global positioning system (GPS) receiver, and further comprising an inertial measurement unit (IMU), wherein the processing logic is configured to correct the motion data received from the GPS receiver using input from the IMU.

F5. The sensor unit of any of paragraphs F0 through F4, wherein the hydrophone is coupled to the hull by a cable, such that the hydrophone is configured to be disposed approximately two meters below a surface of a body of water when the sensor unit is floating freely on the surface.

F6. The sensor unit of any of paragraphs F0 through F5, further comprising a rechargeable battery and a plurality of solar panels coupled to the hull, wherein the battery is configured to be recharged by the solar panels.

F7. The sensor unit of F6, wherein the hull has a frusto-pyramidal upper portion, and the solar panels are coupled to respective flat faces of the upper portion.

G0. A method of determining metocean characteristics of a body of water, the method comprising: establishing remote communication with a plurality of floating metocean sensor units deployed in a body of water, each of the floating metocean sensor units including a hull having an attached hydrophone and enclosing processing logic in communication with the hydrophone and an onboard displacement sensor; receiving wave information from each of the sensor units based on motion of the sensor unit as determined by the displacement sensor; and receiving wind information from each of the sensor units based on the wave information and a measurement of underwater sound using the hydrophone.

G1. The method of G0, wherein establishing remote communication comprises communication via a satellite communication network.

G2. The method of any of paragraphs G0 through G1, wherein the displacement sensor comprises a global positioning system (GPS) receiver.

G3. The method of any of paragraphs G0 through G2, wherein the displacement sensor comprises an inertial measurement unit (IMU).

G4. The method of any of paragraphs G0 through G3, further comprising changing a parameter of at least one of the sensor units from a remote location.

Advantages, Features, and Benefits

The different embodiments and examples of the real-time metocean sensor arrays and related methods described herein provide several advantages over known solutions. For example, illustrative embodiments and examples described herein are low-cost, easy to use, and solar-powered, making a global network of connected wave sensors possible.

Additionally, and among other benefits, illustrative embodiments and examples described herein include an upper clamp ring for securing solar panels, such that the number of screw attachments penetrating the hull is reduced and makes the sensor unit is easier and faster to assemble.

Additionally, and among other benefits, illustrative embodiments and examples described herein allow the sensor unit to be activated and/or deactivated using a handheld magnet, such that the waterproof barrier need not be compromised for this operation.

Additionally, and among other benefits, illustrative embodiments and examples described herein use a refractive lightpipe, which enables the use of a board-mounted LED for the visibility light. This is a very robust and low-cost solution to provide a signaling light on the instrument.

Additionally, and among other benefits, illustrative embodiments and examples described herein include one or more integrated handles for facilitating manual handling of the compact devices.

Additionally, and among other benefits, illustrative embodiments and examples described herein permit accurate in-situ measurement and monitoring of wind information.

Additionally, and among other benefits, illustrative embodiments and examples described herein permit in-situ measurement and monitoring of wind information collocated on a device also measuring in-situ wave and/or current information.

Additionally, and among other benefits, illustrative embodiments and examples described herein include interchangeable, modular electronics enclosures having different features, e.g., different communications packages.

Additionally, and among other benefits, illustrative embodiments and examples described herein include one or more of the following advantages:

- Low cost allows for new types of deployment, empowers new user groups
- Integrated platform allows for remote access and ease of communication with the device, anywhere, any time. The two-way communication between the Web-enabled interface and the instrument enables on-the-fly changes in data transmissions, alerts, and device settings when the device is anywhere in the world.
- Optimized solar panel array allows for indefinite and continuous deployment without need for servicing, lowering the cost of operation as compared to known solutions.
- Data acquisition system maintains excellent accuracy of ocean wave observations when the instrument drifts in strong currents. Existing buoy system makers specifically warn against drifting at high speeds, as it is known to create errors in the data for those systems. Accordingly, the low-pass filtering method described above permits sensor units of the present disclosure to handle high drift speeds where others cannot.
- Lightweight portability allows for system to be deployed by hand from any type of boat.
- Flat bottom design allows the device to rest on a flat surface such as a tabletop or boat deck without needing separate supports.
- Position updates are integrated to enable real-time tracking, proximity warnings, and geofencing.
- Integration of the device with online back and front ends allows for real-time updates and messaging on ocean conditions as they occur.
- Externally mounted solar panels allow water and air to clean and cool the panels automatically, and simplifies the design.
- May be constructed of all marine-grade plastic parts, which can be mass-produced, are low-cost, and extremely durable to the marine environment (e.g., no rust).
- Externally visible user interface provides system status feedback prior to and during deployments.
- The complete user interaction panel (containing connector, SD card, LEDs etc.) is upward facing so the user does not need to disassemble the instrument in order to download data, pre-charge battery, or otherwise interact with it (turn off, firmware upgrade etc.). Simple removal of the cover provides access.

No known system or device can perform these functions. However, not all embodiments and examples described herein provide the same advantages or the same degree of advantage.

Conclusion

The disclosure set forth above may encompass multiple distinct examples with independent utility. Although each of these has been disclosed in its preferred form(s), the specific embodiments thereof as disclosed and illustrated herein are not to be considered in a limiting sense, because numerous variations are possible. To the extent that section headings are used within this disclosure, such headings are for organizational purposes only. The subject matter of the disclosure includes all novel and nonobvious combinations and subcombinations of the various elements, features, functions, and/or properties disclosed herein. The following claims particularly point out certain combinations and subcombinations regarded as novel and nonobvious. Other combinations and subcombinations of features, functions, elements, and/or properties may be claimed in applications claiming priority from this or a related application. Such claims, whether broader, narrower, equal, or different in scope to the original claims, also are regarded as included within the subject matter of the present disclosure.

What is claimed is:

1. A floatable metocean instrument comprising:
a hull having a central cavity, the hull including:
 a symmetrical lower portion extending downward from a midsection of the hull, configured to be submerged when the instrument is deployed in a body of water and to provide a uniform directional response to surface currents and surface waves, and
 a polygonal upper portion extending upward from the midsection of the hull and including a plurality of ribs extending upward from the midsection to define a plurality of substantially planar angled faces;
a plurality of solar panels, each disposed on a respective one of the angled faces of the hull such that the solar panels are external to the instrument and exposed to a local environment; and
an electronics box removably disposed within the central cavity of the hull, the electronics box having a body portion defining an interior enclosure which contains:
 a global positioning system (GPS) receiver,
 a satellite transceiver, and
 a power regulating circuit configured to charge a battery using energy collected by the solar panels; and a battery configured to receive power from the power regulating circuit and to supply power to the GPS receiver and the satellite transceiver;

wherein the GPS receiver is configured to measure positions of the instrument in real time, and the satellite transceiver is configured to transmit information based on the positions of the instrument to a satellite;

wherein the upper portion of the hull includes a clamping ring having an inboard lip and an outboard perimetric flange, wherein the electronics box is suspended from the inboard lip into a central cavity of the hull, and wherein the perimetric flange clamps each of the solar panels against the hull when the clamping ring is fastened to the hull.

2. The instrument of claim 1, wherein the electronics box further contains an inertial measurement unit (IMU) configured to collect motion data, and a digital signal processor configured to use the motion data collected by the IMU to correct measurements made by the GPS receiver.

3. The instrument of claim 1, wherein the electronics box further contains processing logic configured to receive displacement data from the GPS receiver and to transform the displacement data into wave and current information, and wherein the satellite transceiver is configured to transmit the wave and current information to the satellite.

4. The instrument of claim 3, further comprising a hydrophone coupled to the hull.

5. The instrument of claim 4, wherein the processing logic is further configured to receive acoustical data collected by the hydrophone and to transform the acoustical data and the displacement data into wind information, and wherein the satellite transceiver is configured to transmit the wind information to the satellite.

6. The instrument of claim 1, further comprising:
processing logic and a displacement sensor disposed in the central cavity of the hull; and
a hydrophone coupled to the hull;
wherein the processing logic is configured to:
receive acoustic data from the hydrophone and motion data from the GPS receiver;
determine local wave characteristics based on the motion data; and
determine, using a trained neural network, local wind characteristics based on the motion data and the acoustic data.

7. The instrument of claim 6, wherein the trained neural network is configured to combine an acoustic-based wind speed estimate with a wave motion-based wind speed estimate.

8. The instrument of claim 6, further comprising an inertial measurement unit (IMU), wherein the processing logic is configured to correct the motion data received from the GPS receiver using input from the IMU.

9. The instrument of claim 6, wherein the hydrophone is coupled to the hull by a cable, such that the hydrophone is configured to be disposed approximately two meters below a surface of a body of water when the instrument is floating freely on the surface.

10. The instrument of claim 1, wherein the polygonal upper portion is frusto-pyramidal.

11. The instrument of claim 1, wherein the electronics box further contains processing logic configured to receive displacement data from the GPS receiver and to transform the displacement data into a wave-based wind speed estimate, and wherein the satellite transceiver is configured to transmit the wave-based wind speed estimate to the satellite.

12. The instrument of claim 11, wherein the electronics box further contains an inertial measurement unit (IMU) configured to collect motion data, and a digital signal processor configured to use the motion data collected by the IMU to correct measurements made by the GPS receiver.

13. The instrument of claim 12, wherein the processing logic is further configured to receive underwater acoustic data from a hydrophone coupled to the instrument, and to transform the displacement data and the acoustic data into wave, wind, and current information, and wherein the satellite transceiver is further configured to transmit the wave, wind, and current information to the satellite.

14. The instrument of claim 1, wherein the GPS receiver is further configured to measure a velocity of the instrument in real time, and the satellite transceiver is further configured to transmit information based on the velocity of the instrument to a satellite.

15. A floatable metocean instrument comprising:
a hull having a central cavity, the hull including:
a symmetrical lower portion extending downward from a midsection of the hull, configured to be submerged when the instrument is deployed in a body of water and to provide a uniform directional response to surface currents and surface waves, and
a polygonal upper portion extending upward from the midsection of the hull and including a plurality of ribs extending upward from the midsection to define a plurality of substantially planar angled faces;
a plurality of solar panels, each disposed on a respective one of the angled faces of the hull;
an electronics box removably disposed within the central cavity of the hull, the electronics box having a body portion defining an interior enclosure which contains:
a global positioning system (GPS) receiver,
a satellite transceiver, and
a power regulating circuit configured to charge a battery using energy collected by the solar panels;
a clamping ring included in the upper portion of the hull, the clamping ring having an inboard lip and an outboard perimetric flange, wherein the electronics box is suspended from the inboard lip into a central cavity of the hull, and wherein the perimetric flange clamps each of the solar panels against the hull when the clamping ring is fastened to the hull; and
a battery configured to receive power from the power regulating circuit and to supply power to the GPS receiver and the satellite transceiver;
wherein the GPS receiver is configured to measure positions of the instrument in real time, and the satellite transceiver is configured to transmit information based on the positions of the instrument to a satellite.

16. The instrument of claim 15, wherein the plurality of solar panels are each disposed on a respective one of the angled faces of the hull such that the solar panels are external to the instrument and exposed to a local environment.

* * * * *